(12) United States Patent
Pan

(10) Patent No.: US 10,973,859 B2
(45) Date of Patent: *Apr. 13, 2021

(54) COMPOSITIONS COMPRISING UNSATURATED FATTY ACIDS AND NITRIC OXIDE RELEASING COMPOUNDS AND USE THEREOF FOR ENHANCING COGNITIVE AND RELATED FUNCTIONS

(71) Applicant: NESTEC S.A., Vevey (CH)

(72) Inventor: Yuanlong Pan, Chesterfield, MO (US)

(73) Assignee: SOCIÉTÉ DES PRODUITS NESTLÉ S. A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/150,979

(22) Filed: Oct. 3, 2018

(65) Prior Publication Data

US 2019/0030088 A1 Jan. 31, 2019

Related U.S. Application Data

(63) Continuation of application No. 15/440,702, filed on Feb. 23, 2017, now Pat. No. 10,111,911, which is a continuation-in-part of application No. 12/734,013, filed as application No. PCT/US2008/013870 on Dec. 19, 2008, now abandoned.

(60) Provisional application No. 61/010,097, filed on Jan. 4, 2008, provisional application No. 61/137,382, filed on Jul. 30, 2008.

(51) Int. Cl.

| A61K 35/60 | (2006.01) |
|---|---|
| A61K 45/06 | (2006.01) |
| A23D 9/007 | (2006.01) |
| A61K 31/522 | (2006.01) |
| A61K 31/454 | (2006.01) |
| A23K 50/40 | (2016.01) |
| A61K 31/22 | (2006.01) |
| A61K 31/20 | (2006.01) |
| A61K 31/445 | (2006.01) |
| A23K 20/158 | (2016.01) |
| A23L 33/12 | (2016.01) |
| A61K 31/4375 | (2006.01) |
| A23L 33/115 | (2016.01) |
| A23L 33/175 | (2016.01) |
| A23K 10/18 | (2016.01) |
| A61K 31/55 | (2006.01) |
| A61K 36/16 | (2006.01) |
| A61K 31/683 | (2006.01) |
| A61K 31/675 | (2006.01) |
| A61K 31/54 | (2006.01) |
| A61K 31/56 | (2006.01) |
| A61K 31/663 | (2006.01) |
| A61K 31/198 | (2006.01) |
| A61K 31/202 | (2006.01) |

(52) U.S. Cl.
CPC .............. *A61K 35/60* (2013.01); *A23D 9/007* (2013.01); *A23K 10/18* (2016.05); *A23K 20/158* (2016.05); *A23K 50/40* (2016.05); *A23L 33/115* (2016.08); *A23L 33/12* (2016.08); *A23L 33/175* (2016.08); *A61K 31/198* (2013.01); *A61K 31/20* (2013.01); *A61K 31/202* (2013.01); *A61K 31/22* (2013.01); *A61K 31/4375* (2013.01); *A61K 31/445* (2013.01); *A61K 31/454* (2013.01); *A61K 31/522* (2013.01); *A61K 31/54* (2013.01); *A61K 31/55* (2013.01); *A61K 31/56* (2013.01); *A61K 31/663* (2013.01); *A61K 31/675* (2013.01); *A61K 31/683* (2013.01); *A61K 36/16* (2013.01); *A61K 45/06* (2013.01)

(58) Field of Classification Search
CPC ................................ A61K 31/20; A61K 25/28
USPC ........................................................ 514/560
See application file for complete search history.

(56) References Cited

U.S. PATENT DOCUMENTS

| 5,750,572 | A | 5/1998 | Bruzzese |
|---|---|---|---|
| 5,874,471 | A | 2/1999 | Waugh |
| 6,951,658 | B1 | 10/2005 | Pearson et al. |
| 6,964,969 | B2 | 11/2005 | McCleary |
| 7,135,498 | B1 | 11/2006 | Chopp |

(Continued)

FOREIGN PATENT DOCUMENTS

| EP | 0652012 A1 | 5/1995 |
|---|---|---|
| EP | 0832652 | 4/1998 |

(Continued)

OTHER PUBLICATIONS

"Supplemental Citrulline Is More Efficient Than Arginine in Increasing Systemic Arginine Availability in Mice1-3 Umang", Agarwal et al., The Journal of Nutrition Nutrient Requirements and Optimal Nutrition. First published online Feb. 8, 2017; doi:10.3945/jn.116.240382. (Year: 2017).*

(Continued)

*Primary Examiner* — Michael Barker
*Assistant Examiner* — Deborah A Davis
(74) *Attorney, Agent, or Firm* — K&L Gates LLP

(57) ABSTRACT

Compositions include arginine and one or more unsaturated fatty acids. Methods for using such compositions can enhance cognitive function, reduce or prevent a decline of social interaction, reduce or prevent age-related behavioral changes, increase trainability, maintain optimal brain function, facilitate learning and memory, reduce memory loss, retard brain aging, prevent or treat strokes, and/or prevent or treat dementia in an animal. Preferably, the compositions are food compositions useful for enhancing cognitive function in humans and companion animals.

20 Claims, 3 Drawing Sheets

(56) References Cited

U.S. PATENT DOCUMENTS

| | | | |
|---|---|---|---|
| 2003/0073747 | A1 | 4/2003 | Gross et al. |
| 2003/0180406 | A1 | 9/2003 | Sies |
| 2004/0043013 | A1* | 3/2004 | McCleary .............. A61K 45/06 424/94.1 |
| 2005/0002992 | A1 | 1/2005 | McCleary et al. |
| 2006/0002985 | A1 | 1/2006 | Zicker et al. |
| 2006/0014773 | A1* | 1/2006 | McCleary .............. A61K 36/16 514/283 |
| 2006/0166935 | A1 | 7/2006 | Bryhn |
| 2007/0060651 | A1 | 3/2007 | Larson et al. |

FOREIGN PATENT DOCUMENTS

| | | |
|---|---|---|
| EP | 1378236 | 1/2004 |
| EP | 1634599 | 1/2004 |
| EP | 1074252 B1 | 12/2005 |
| EP | 1665940 | 6/2006 |
| EP | 1698685 A1 | 9/2006 |
| EP | 1955698 A1 | 8/2008 |
| GB | 2268871 | 1/1994 |
| WO | 9625861 A1 | 8/1996 |
| WO | 03041701 A2 | 5/2003 |
| WO | 2004082402 A1 | 9/2004 |
| WO | 2004100896 A2 | 11/2004 |
| WO | 2005006877 A1 | 1/2005 |
| WO | 2006071919 A2 | 7/2006 |
| WO | 2006072084 A2 | 7/2006 |
| WO | 2006074089 A2 | 7/2006 |
| WO | 2007008586 A2 | 1/2007 |
| WO | 200704148 | 4/2007 |
| WO | 2007041418 | 4/2007 |
| WO | 2007073178 A2 | 6/2007 |
| WO | 2009045481 A1 | 4/2009 |

OTHER PUBLICATIONS

Jingyao, et al. "Studies in Antiaging Effects of Fish Oil", Chinese Journal of Marine Drugs, (1):51-54, 1999, in Chinese, published in 1999.

Tao Wen-qin "Research Progress in the Role of Nitric Oxide in Learning and Memory", J, of Guangzhou Normal Univ, (Nat. Sci, Ed.), 51(5):32-35, 2000, in Chinese, pub. in 2000.

Tapp et al., "Size and Reversal Learning in the Beagle Dog as a Measure of Executive Function and Inhibitory Control in Aging", Learning & Memory, vol. 10, 2003, pp. 64-73.

Cotman et al., "Exercise: a behavioral intervention to enhance brain health and plasticity", Trends in Neurosciences, vol. 25, No. Jun. 6, 2002, pp. 295-301.

Dimakopoulos et al., "Aspects of Neurodegeneration in the Canine Brain", The Journal of Nutrition, vol. 132, No. 6, Jun. 1, 2002, pp. 1579S-1582S.

Cummings et al., "β-amyloid deposition and other measures of neuropathology predict cognitive status in Alzheimer's disease", Neurobiology of Aging, vol. 17, No. 6, Nov.-Dec. 1996, pp, 921-933.

Young et al., "Omega-3 Fatty Acids and Neuropsychiatric Disorders", Reproduction Nutrition Development, vol. 45, Issue No. 1, Jan. 1, 2005, pp. 1-28.

Song et al., "Omega-3 Fatty Acid Ethyl-Eicosapentaenoate, but not Soybean Oil, Attenuates Memory Impairment Induced by Central IL-1 Beta Administration", Journal of Lipid Research, vol. 45, 2004, pp. 1112-1121.

Ohtsuka, "Effect of Oral Administration of L-Arginine On Senile Dementia", The American Journal of Medicine, vol. 108, Issue No. 5, Apr. 1, 2000, p. 439.

Sydenham et al., "Omega 3 Fatty Acid for the Prevention of Cognitive Decline and Dementia", Cochrane Database Systematic Reviews, Jun. 2012, pp. 1-40.

"Recommended Daily Intakes and Upper Limits for Vitamin and Minerals", ConsumerLab.com, Aug. 31, 2020, 5 pages.

Bazan, "Docosahexaenoic Acid Signaling-Mediated Neuroprotection: Significance in Alzheimer's Disease", PUFA Newsletter, vol. 11, Issue No. 2, Jun. 2006, pp. 1-21.

Priority Document of U.S. Appl. No. 61/010,097, dated Jan. 4, 2008, pp. 1-39.

Priority Document of U.S. Appl. No. 61/137,382, dated Jul. 30, 2008, pp. 1-42.

* cited by examiner

FIG. 1

Table 1

| (uM) | low | normal | high |
|---|---|---|---|
| DHA | 0.15 | 1.5 | 15 |
| Arginine | 1.5 | 15 | 150 |
| Citrulline | 1.5 | 15 | 150 |

COMPOSITIONS COMPRISING UNSATURATED FATTY ACIDS AND NITRIC OXIDE RELEASING COMPOUNDS AND USE THEREOF FOR ENHANCING COGNITIVE AND RELATED FUNCTIONS

CROSS REFERENCE TO RELATED APPLICATIONS

This application is a continuation of U.S. patent application Ser. No. 15/440,702 filed Feb. 23, 2017, which is a continuation-in-part of U.S. patent application Ser. No. 12/734,013 filed on Apr. 1, 2010, with is a national stage application under 35 U.S.C. § 371 of PCT/US2008/013870 filed Dec. 19, 2008, which claims priority to U.S. Provisional App. Ser. No. 61/010,097 filed Jan. 4, 2008 and U.S. Provisional App. Ser. No. 61/137,382 filed Jul. 30, 2008, the entire disclosures of which are incorporated herein by reference.

BACKGROUND OF THE INVENTION

Field of the Invention

The present disclosure relates generally to compositions and methods for enhancing cognitive function and particularly to compositions comprising unsaturated fatty acids and nitric oxide releasing compounds and their use for enhancing cognitive function in animals.

Description of Related Art

Aged or aging animals frequently suffer some degree of cognitive impairment. Changes, including decline in cognitive function that progresses with age, and age-related changes in brain morphology and cerebrovascular function are commonly observed, e.g., brain aging. Age-related or age-associated cognitive impairment may manifest itself in many ways, e.g., short-term memory loss, diminished capacity to learn, diminished rate of learning, diminished attention, diminished motor performance, and/or dementia, among other indicia. In some cases, a specific etiology of such cognitive decline is unknown. In other cases, cognitive impairment results from the onset or progression of recognized diseases, disorders, or syndromes, for example, Alzheimer's disease (AD). It is known that age-associated cognitive decline is distinct from and can occur independently of AD.

Animal models of cognitive impairment greatly facilitate the study of such conditions including their physiology, neurology, anatomy, and pathology, Dogs are useful model animals that demonstrate age-associated cognitive decline in learning and memory that varies depending on the function of the cognitive task (Adams B et al., 2000a; Chan A D F et al., 2002; Su M-Y et al., 1998; and, Tapp P D et al., 2003). While the study of such decline in dogs is useful in its own right because of their role as companion animals, the fact that the observed decline mirrors age-related cognitive declines seen in humans (Adams B et al. 2000b) makes the studies even more valuable. Aged dogs develop neuropathology that is related to that seen in both successfully aging humans and patients with AD, such as beta amyloid protein (Cotman C W and Berchtold, 2002; and Cummings B J et al., 1996). However, dogs do not demonstrate every hallmark of AD, in particular, tau-containing neurofibrillar tangles (Dimakopoulos A C et al., 2002) have not been observed. Therefore, the condition in dogs is distinct and referred to as Canine Cognitive Dysfunction Syndrome (CCDS).

Both healthy dogs and unhealthy dogs such as those diagnosed with CCDS may present clinically with progressive cognitive impairment and neuropathological changes (London E D et al., 1983). In addition, aging dogs and those diagnosed with CCDS exhibit various behavioral disorders. For example, they may not respond to their name or familiar commands, may get lost or confused even in familiar surroundings, may no longer greet or respond to their owners or visitors, may exhibit diminished daytime activity, may walk in circles, may shun affection, and may lose bladder or bowel control.

Though advances have been made, there remains a need to develop compositions and methods that improve cognition, particularly in aging humans and other animals. Compositions and methods for the treatment and/or prevention of cognitive impairment, neurodegeneration conditions, stroke, and dementia are also needed. Such therapies would be useful to improve the overall quality of life for all involved. For companion animals, these therapies would lead to improved owner satisfaction and would improve the owner-companion animal bond.

SUMMARY

It is, therefore, an object of the present disclosure to provide compositions and methods useful for enhancing cognitive function in an animal.

It is another object of the present disclosure to provide methods for reducing or preventing a decline of social interaction, reducing or preventing age-related behavioral changes, increasing trainability, maintaining optimal brain function, facilitating learning and memory, reducing memory loss, retarding brain aging, preventing or treating strokes, and preventing or treating dementia in an animal.

It is a further object of the present disclosure to provide articles of manufacture in the form of kits that contain one or more of the compounds useful to produce the composition of the present disclosure in combination with foods or other ingredients and devices useful for enhancing cognitive function in an animal.

It is another object of the present disclosure to provide a package comprising a composition of the present disclosure and a label affixed to the package indicating the contents of the package and/or the benefits of administering the composition to an animal.

One or more of these other objects are achieved using novel compositions and methods for enhancing cognitive function. Generally, the compositions comprise one or more unsaturated fatty acids and nitric oxide releasing compounds. The methods generally comprise administering the compositions in an amount effective for enhancing cognitive function, particularly to prevent, reduce and/or delay the age-related cognitive-decline, cognitive impairment, neurodegeneration conditions, stroke, and dementia in an animal.

Other and further objects, features, and advantages of the present disclosure will be readily apparent to those skilled in the art.

BRIEF DESCRIPTION OF THE DRAWINGS

FIG. 1 is a table setting forth the parameters of an experimental study disclosed herein as Example 3.

DETAILED DESCRIPTION OF THE INVENTION

Definitions

Figure 2:
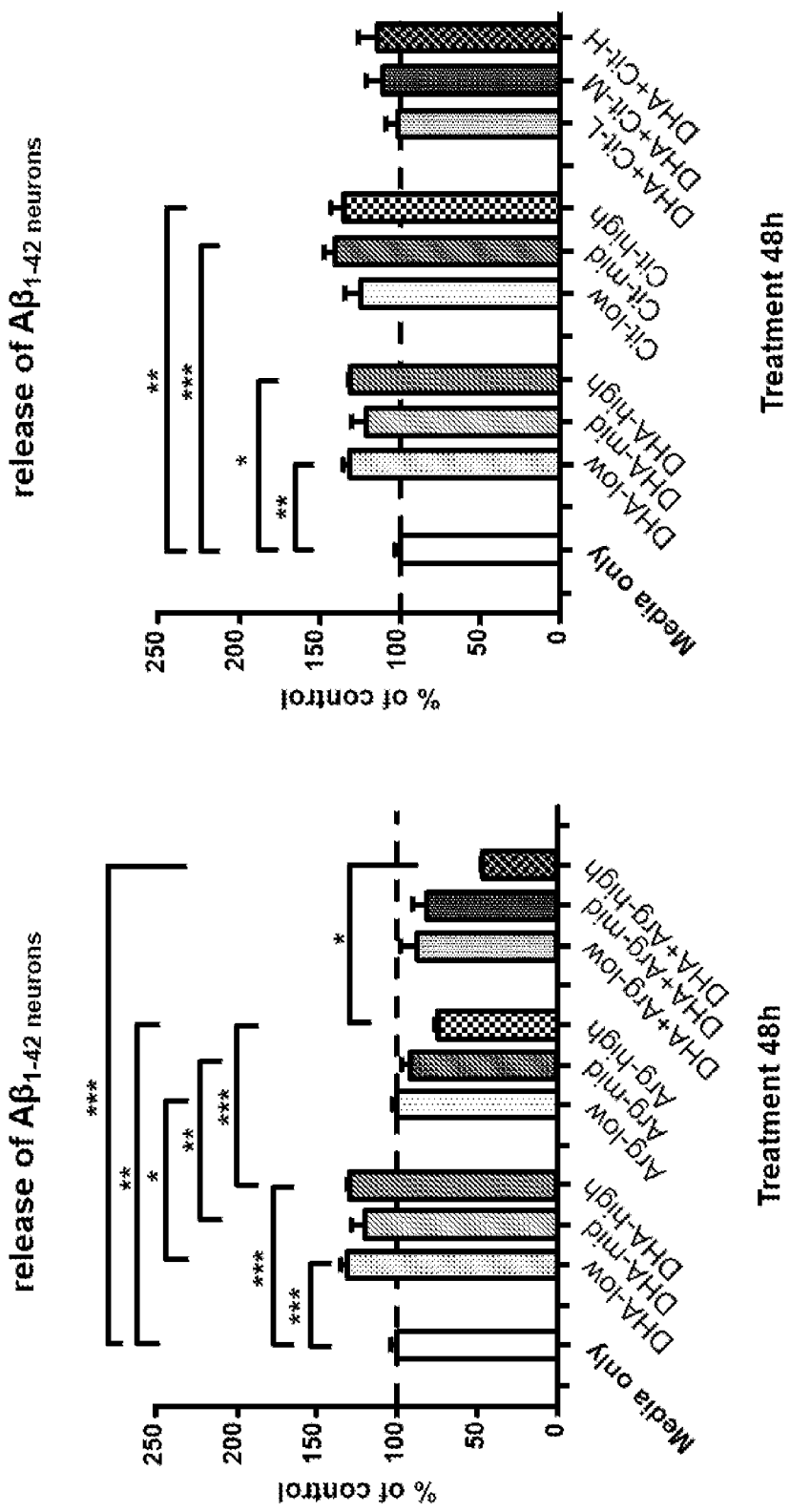
FIG. 2 contains graphs depicting results regarding neurons from the experimental study disclosed herein as Example 3.

The following abbreviations may be used herein: AA, arachidonic acid; ALA, alpha-linolenic acid; ANOVA, analysis of variance; DHA, docosahexaenoic acid; DPA, docosapentaenoic acid; EPA, eicosapentaenoic acid; LA, linoleic acid; UFA, unsaturated fatty acids (as used herein UFA refers to one or more such fatty acids); NO, nitric oxide; NORC, nitric oxide releasing compound or compounds; and L-Arg, L-arginine.

The term "animal" means any animal that could benefit from one or more of the methods of the present disclosure including enhancing cognitive function; altering cognitive, motor, or behavioral function; reducing or preventing a decline of social interaction; reducing or preventing age-related behavioral changes; increasing trainability; maintaining optimal brain function; facilitating learning and memory; reducing memory loss; retarding brain aging; preventing or treating strokes; preventing or treating dementia; and/or maintaining mental clarity and alertness. Generally, the animal is a human, avian, bovine, canine, equine, feline, hircine, lupine, murine, ovine, and porcine animal. Preferably, the term "animal" means an animal for which an enhancement of cognitive function is desired or would benefit from an improvement in cognitive function. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the animal is a human or a companion animal such as a dog or cat.

The term "enhancing cognitive function" means one or more of increasing cognitive, motor, or behavioral function in an animal or preventing, reducing, or delaying a decline in cognitive, motor, or behavioral function in an animal.

The term "unsaturated fatty acids" or "UFA" means polyunsaturated fatty acids or monounsaturated fatty acids, including monocarboxylic acids having at least one double bond. UFAs include (n–6) fatty acids such as linoleic acid (LA) and arachidonic acid (AA) and (n–3) fatty acids such as eicosapentaenoic acid (EPA), alpha-linolenic acid (ALA), docosapentaenoic acid (DPA) and docosahexaenoic acid (DHA). UFAs also include myristoleic acid, palmitoleic acid, oleic acid, linoleic acid, cis-vaccenic acid, and erucic acid.

The term "fish oil" means a fatty or oily extract, relatively rich in UFA, whether crude or purified, obtained from a sea animal, preferably a cold-water fish such as, but not limited to, salmon, tuna, mackerel, herring, sea bass, striped bass, halibut, catfish, and sardines, as well as shark, shrimp, and clams, or any combination thereof. Fish oil is generally a term of art used by ingredient suppliers and encompasses a range or products of varying UFA content and purity.

The term "nitric oxide releasing compounds" or "NORC" means any compound or compounds that cause or can result in the release of nitric oxide in an animal. Examples of such compounds include L-arginine, L-arginine-containing peptides and proteins, and analogs or derivatives thereof that are known or determined to release nitric oxide, such as arginne alpha-ketoglutarate, GEA 3175, sodium nitroprusside, glyceryl trinitrate, S-nitroso-N-acetyl-penicillamine, nitroglycerin, S—NO-glutathione, NO-conjugated non-steroidal anti-inflammatory drugs (e.g., NO-naproxen, NO-aspirin, NO-ibuprofen, NO-Diclofenac, NO-Flurbiprofen, and NO-Ketoprofen), NO-releasing compound-7, NO-releasing compound-5, NO-releasing compound-12, NO-releasing compound-18, diazenium diolates and derivatives thereof, diethylamine NONOate, and any organic or inorganic compound, biomolecule, or analog, homolog, conjugate, or derivative thereof that causes the release of nitric oxide, particularly "free" NO, in an animal. NORC is also defined to include supplements that can be converted to nitric oxide releasing compounds when metabolized in the body, e.g., citrulline and ornithine.

The term "effective amount" means an amount of a compound, material, composition, medicament, or other material that is effective to achieve a particular biological result. Such results include, but are not limited to, one or more of the following: enhancing cognitive function, increasing daytime activity, improving learning (either the rate or ease of learning), improving attention, improving social behavior, improving motor performance, and/or improving cerebrovascular function, particularly in aging animals. In various embodiments, "effective amount" refers to an amount suitable to prevent a decline in any one or more of the above qualities, or, in certain embodiments, to improve any one or more of the above qualities, for example, cognitive function or performance, learning rate or ability, problem solving ability, attention span and ability to focus on a task or problem, motor function or performance, social behavior, and the like. In other embodiments, an effective amount is suitable to reduce either the extent or rate of decline in an animal's cognitive skills or functioning, and/or the effective amount is suitable to delay the onset of such decline. Such effectiveness may be achieved, for example, by administering the compositions of the present disclosure to an animal or to a population of animals. Preferably the prevention, reduction, or delay of such a decline, or the improvement in an individual or population is relative to a cohort, e.g., a control animal or a cohort population that has not received the treatment, or been administered the composition or medicament.

The term "cognitive function" refers to the special, normal, or proper physiologic activity of the brain, including one or more of the following: mental stability, memory/recall abilities, problem solving abilities, reasoning abilities, thinking abilities, judging abilities, ability to discriminate or make choices, capacity for learning, ease of learning, perception, intuition, attention, and awareness. "Enhanced cognitive function" or "improved cognitive function" refers to any improvement in the special, normal, or proper physiologic activity of the brain, including one or more of the following: mental stability, memory/recall abilities, problem solving abilities, reasoning abilities, thinking abilities, judging abilities, ability to discriminate or make choices, capacity for learning, ease of learning, perception, intuition, attention, and awareness, as measured by any means suitable in the art.

The term "behavior" means anything that an animal does in response or reaction to a given stimulation or set of conditions. "Enhanced behavior" or "improved behavior" means any improvement in anything that an animal does in response or reaction to a given stimulation or set of conditions. "Behavior" is used synonymously with "behavioral function" herein.

The term "motor function" or "motor performance" means the biological activity of the tissues that affect or produce movement in an animal. Such tissue include, without limitation, muscles and motor neurons. "Enhanced motor performance (or function)" or "improved motor performance (or function)" refers to any improvement in the biological activity of the tissues that affect or produce movement in an animal.

The term "decline" of any of the foregoing categories or specific types of qualities or functions in an individual (phenotypes) is generally the opposite of an improvement or enhancement in the-quality or function. An "effective amount" of a composition may be an amount required to prevent decline altogether or to substantially prevent decline ("prevent" decline), to reduce the extent or rate of decline ("reduce" decline) over any time course or at any time point, or delay the onset, extent, or progression of a decline ("delay" a decline). Prevention, reduction, or delay of "decline" is frequently a more useful comparative basis when working with non-diseased aging animals (e.g., "healthy aging animals"). Prevention, reduction, and delay can be considered relative to a control or cohort which does not receive the treatment, for example, the diet or supplement of interest. Prevention, reduction, or delay of either the onset of a detrimental quality or condition, or of the rate of decline in a particular function can be measured and considered on an individual basis, or in some embodiments on a population basis. The net effect of preventing, reducing, or delaying decline is to have less decrease in cognitive, motor, or behavioral functioning per unit time, or at a given end point. In other words, ideally, for an individual or in a population, cognitive, motor, and behavioral functioning is maintained at the highest possible level for the longest possible time. Thus, a net increase in cognitive, motor, or behavioral function is not required for any embodiment. For purposes herein, an individual can be compared to a control individual, group, or population. A population can likewise be compared to an actual individual, to normalized measurements for an individual, or to a group or population, as is useful.

The term "aging" means being of advanced age such that the animal has exceeded 50% of the average lifespan for its particular species and/or breed within a species. For example, if the average lifespan for a given breed of dog is 10 years, then a dog within that breed greater than 5 years old would be considered "aging" for purposes herein. "Healthy aging animals" are those with no known diseases, particularly diseases relating to loss of cognitive impairment such as might confound the results. In studies using healthy aging animals, cohort animals are preferably also healthy aging animals, although other healthy animals with suitable cognitive, motor, or behavioral functioning may be suitable for use as comparative specimens. If animals with specific disease diagnoses, or cognitive, motor, or behavioral limitations are used, then the cohort animals should include animals that are similarly diagnosed, or which present with similar indicia of the disease or cognitive, motor, or behavioral limitation.

The term "food" or "food product" or "food composition" means a product or composition that is intended for ingestion by an animal, including a human, and provides nutrition to the animal.

As used herein, a "food product formulated for human consumption" is any composition specifically intended for ingestion by a human being. The term "pet food" or "pet food composition" means a composition intended for consumption by animals, preferably by companion animals. A "complete and nutritionally balanced pet food" is one that contains all known required nutrients for the intended recipient or consumer of the food, in appropriate amounts and proportions, based for example on recommendations of recognized authorities in the field of companion animal nutrition. Such foods are therefore capable of serving as a sole source of dietary intake to maintain life or promote production, without the addition of supplemental nutritional sources. Nutritionally balanced pet food compositions are widely known and used in the art. The term includes any food, feed, snack, food supplement, treat, meal substitute, or meal replacement, whether intended for a human or another animal. Animal food includes food or feed intended for any domesticated or wild species. In preferred embodiments, a food for an animal represents a nutritionally complete food composition, e.g., a pelleted, extruded, or dry food. Examples of such animal foods include extruded pet foods, such as foods for dogs and cats.

The term "dietary supplement" means a product that is intended to be ingested in addition to the normal animal diet. Dietary supplements may be in any form, e.g., solid, liquid, gel, tablets, capsules, powder, and the like. Preferably they are provided in convenient dosage forms. In some embodiments they are provided in bulk consumer packages such as bulk powders, liquids, gels, or oils. In other embodiments, supplements are provided in bulk quantities to be included in other food items such as snacks, treats, supplement bars, beverages and the like.

The term "long-term administration" means periods of repeated administration or consumption in excess of one month. Periods of longer than two, three, or four months are preferred for certain embodiments. Also preferred are more extended periods that include longer than 5, 6, 7, 8, 9, or 10 months. Periods in excess of 11 months or 1 year are also preferred. Longer term use extending over 1, 2, 3, or more years are included in the present disclosure. For certain aging animals, the animal will continue consuming on a regular basis for the remainder of its life. Sometimes this is referred to as consumption for "extended" periods.

The term "regular basis" means at least monthly dosing with the compositions or consumption of the compositions, more preferably weekly dosing. More frequent dosing or consumption, such as twice, three, or seven times weekly, is preferred in certain embodiments. Still more preferred are regimens that comprise at least once daily consumption. The skilled artisan will appreciate that the blood level of a compound or certain metabolites of that compound or which result after the consumption of that compound, may be a useful tool for assessing or determining dosing frequency. A frequency, regardless of whether expressly exemplified herein, that allows maintenance of a desired blood level of the measured compound within acceptable ranges is useful herein. The skilled artisan will appreciate that dosing frequency will be a function of the composition that is being consumed or administered, and some compositions may require more or less frequent administration to maintain a desired blood level of the measured compound.

The term "oral administration" or "orally administering" means that the animal ingests, or a human is directed to feed, or does feed, the animal one or more of the compositions described herein. Wherein a human is directed to feed the composition, such direction may be that which instructs and/or informs the human that use of the composition may and/or will provide the referenced benefit, for example, enhancing cognitive function, improving liver function, increasing daytime activity, improving learning, improving attention, improving social behavior, improving motor performance, and/or improving cerebrovascular function, or preventing, reducing, or delaying a decline in such foregoing functions or qualities. Such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., internet, electronic mail, website, or other computer-related media), and/or packaging associated with the composition (e.g., a label present on a container holding the composition), or a combination thereof (e.g., label or package insert with directions to access a website for more information).

The term "cognitive drugs" means any compound, composition, or drug useful for affecting cognitive function, e.g., monoamine oxidase B inhibitors such as selegiline; vasodilators such as nicerogoline and vinpocetine; phosphatidylserine; propentofyline; anticholinesterases (cholinesterase inhibitors) such as tacrine, galantamine, rivastigmine, vinpocetine, donepezil (ARICEPT® (donepezil hydrochloride)), metrifonate, and physostigmine; lecithin; choline cholinomimetics such as milameline and xanomeline; ionotropic N-methyl-D-aspartate (NMDA) receptor antagonists such as memantine; anti-inflammatory drugs such as prednisolone, diclofenac, indomethacin, propentofyline, naproxen, rofecoxin, ibruprofen and suldinac; metal chelating agents such as cliquinol; *Ginkgo biloba*; bisphosphonates; selective oestrogen receptor modulators such as raloxifene and estrogen; a phytoestrogen; beta and gamma secretase inhibitors; cholesterol-lowering drugs such as statins; calcitonin; risedronate; alendronate; and combinations thereof.

The term "in conjunction" means that a composition comprising UFA, NORC, a food composition, cognitive drug, or other compound or composition of the present disclosure are administered to an animal (1) together in a food composition or (2) separately at the same or different frequency using the same or different administration routes at about the same time or periodically. "Periodically" means that the agent is administered on a dosage schedule acceptable for a specific agent and that the food is fed to an animal routinely as appropriate for the particular animal. "About the same time" generally means that the food and agent are administered at the same time or within about 72 hours of each other. "In conjunction" specifically includes administration schemes wherein a cognitive drug is administered for a prescribed period and the compositions comprising UFA and NORC are administered indefinitely.

The term "individual" when referring to an animal means an individual animal of any species or kind.

The term "microorganism" encompasses at least bacteria, molds and other fungi, and yeasts. Probiotics are beneficial microorganisms that can survive or even multiply and thrive in the gastrointestinal tract of an animal. Probiotics can contribute to the overall health of an animal generally and particularly to the gastrointestinal health of the animal.

The term "single package" means that the components of a kit are physically associated, in or with one or more containers, and considered a unit for manufacture, distribution, sale, or use. Containers include, but are not limited to, bags, boxes or cartons, bottles, packages of any type or design or material, over-wrap, shrink-wrap, affixed components (e.g., stapled, adhered, or the like), or combinations of any of the foregoing. For example, a single package kit may provide containers of individual compositions and/or food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain, for example, instructions on how to use the kit, or safety or technical information about one or more components of a kit. Examples of information that can be provided as part of a virtual kit include instructions for use; safety information such as material safety data sheets; poison control information; information on potential adverse reactions; clinical study results; dietary information such as food composition or caloric composition; general information on cognitive, behavioral, or motor function; diseases that effect cognitive, behavioral, or motor function; treating cognitive, behavioral, or motor function; or general information on treatment or preservation of cognitive, behavioral, or motor function; self-help relating to cognitive, behavioral, or motor function; caregiver information for those caring for animals with cognitive, behavioral, or motor function challenges; and use, benefits, and potential side-effects or counter-indications for cognitive drugs.

The term "health and wellness of an animal" means the complete physical, mental, and social well being of the animal, not merely the absence of disease or infirmity.

The term "extending the prime" means extending the number of years an animal lives a healthy life and not just extending the number of years an animal lives, e.g., an animal would be healthy in the prime of its life for a relatively longer time.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed.

As used throughout, ranges are used herein in shorthand, so as to avoid having to set out at length and describe each and every value within the range. Any appropriate value within the range can be selected, where appropriate, as the upper value, lower value, or the terminus of the range.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a puppy", "a method", or "a food" includes a plurality of such "puppies", "methods", or "foods". Reference herein, for example to "an antioxidant" includes a plurality of such antioxidants, whereas reference to "pieces" includes a single piece. Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Where used herein the term "examples," particularly when followed by a listing of terms is merely exemplary and illustrative, and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the present disclosure, or in the field(s) where the term is used. Although any compositions, methods, articles of manufacture, or other means or materials similar or equivalent to those described herein can be used in the practice of the present disclosure, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not cited fully within the specification are set forth at the end of the specification.

Preferred Embodiments

In one aspect, the present disclosure provides compositions suitable for enhancing cognitive function in an animal. The compositions comprise one or more unsaturated fatty acids (UFA) and one or more nitric oxide releasing compounds (NORC) in an amount effective for enhancing cognitive function in an animal. In certain embodiments, the compositions further comprise one or more B vitamins, one or more antioxidants, or combinations thereof. The present disclosure is based upon the discovery that compositions comprising UFA and NORC, with or without B vitamins and/or antioxidants, are effective for enhancing cognitive function in animals. The compositions are useful for affecting one or more cognitive, motor, or behavioral functions in animals regardless of health or age, e.g., juvenile, adult, or senior animals. The compositions increase one or more cognitive, motor, or behavioral functions in animals, including healthy animals of all ages or animals that are susceptible to or suffering from a decline in cognitive function brought about by the aging process or by disease. Similarly, the compositions prevent, reduce, or delay a decline in cognitive function in animals, particularly aging animals susceptible to or suffering from a decline in cognitive function brought about by the aging process or by disease. The compositions are particularly effective for reducing or delaying the effects of age-related and disease-related cognitive decline in humans and companion animals, particularly dogs and cats. The compositions are also useful for enhancing cognitive function when cognitive decline is caused by changes in brain function, particularly brain aging, or damage from disease, particularly strokes.

The UFA can be any UFA suitable for administration to an animal. UFAs can be obtained from any suitable source, synthetic or natural. Preferred sources of UFA are natural sources of such fatty acids and include, without limitation, primrose; dark green vegetables such as spinach; algae and blue-green algae such as *spirulina*; plant seeds and oils from plants such as flax, canola, soybean, walnut, pumpkin, safflower, sesame, wheat germ, sunflower, corn, and hemp; and fish such as salmon, tuna, mackerel, herring, sea bass, striped bass, halibut, catfish, sardines, shark, shrimp, and clams; and the extracted oils of any one or more of the foregoing. The UFA may also be synthetic, and as such may be produced according to any means suitable in the art, from any suitable starting material. The UFA may comprise a blend of any one or more UFA from any one or more sources, such as those exemplified above, whether natural or synthetic. In preferred embodiments, the UFA are long chain polyunsaturated fatty acids (LC-PUFA) comprising one or more monocarboxylic acids having at least 20 carbon atoms and at least two double bonds. Preferably, the UFAs are (n–6) fatty acids or (n–3) fatty acids, most preferably n-3 LC-PUFAs.

The NORC can be any NORC suitable for administration to an animal. NORC can be obtained from any suitable source, synthetic or natural. In various embodiments, the NORC comprises arginine. Presently preferred sources of arginine include, without limitation, animal and plant proteins. Examples of plants considered rich in arginine content and suitable for use herein include, but are not limited to, legumes such as soy, lupins, and carob; grains such as wheat and rice; and fruits such as grapes. Seeds and nuts of plants such as cacao and peanut are also considered rich in arginine content and are therefore useful herein. Some examples of suitable animal proteins considered rich in arginine content are poultry and fish products. The NORC can also be synthetically produced, according to any suitable means in the art. As with UFA, the NORC content of any composition disclosed herein can include a blend of any natural or synthetic NORC. Both UFA and NORC, whether natural or synthetic, can be obtained directly or provided by a commercial source.

In one aspect, the compositions further comprise one or more B vitamins, one or more antioxidants, or combinations thereof. The B vitamins can be any B vitamin suitable for administration to an animal. B vitamins include vitamins B 1 (thiamine), B2 (riboflavin), B3 (aka P or PP) (niacin, including nicotinic acid and/or nicotinamide), B5 (pantothenic acid), B6 (pyridoxine), B7 (aka H) (biotin), B8 (myo-inositol), B9 (aka M or B-c) (folic acid), B12 (cobalamin), or salts, conjugates, or derivatives thereof recognized of found to have B vitamin activity. Combinations of any of the foregoing are also useful herein and are sometimes referred to herein as "mixtures" of B vitamins. Since the vitamin requirements vary for different species, not all of the listed compounds are deemed vitamins for all species. For example, since it is known that myo-inositol can be synthesized by humans, it is no longer deemed a vitamin, as it is not required for adequate human nutrition.

The antioxidants can be any antioxidant suitable for administration to an animal. Antioxidants are well known in the art, particularly the art of food technology and food formulation. Natural antioxidant compounds include vitamins (such as A, C and E, and derivative, conjugates, or analogs thereof), as well as plant extracts, including extracts from fruit, vegetables, herbs, seeds, and other types and/or parts of plants. Compounds such as -lipoic acid, chlorophyll and derivatives thereof, glutathione, ubiquinols (e.g., coenzyme Q10), carotenoids (e.g., lycopene), flavonoids, phenolic acids and polyphenols, and pycnogenol are known to be excellent antioxidants. Some examples of plant sources of antioxidants include those from fruits such as berries (cherry, blackberry, strawberry, raspberry, crowberry, blueberry, bilberry/wild blueberry, black currant), pomegranate, grape, orange, plum, pineapple, kiwi fruit, and grapefruit; those from vegetables including kale, chili pepper, red cabbage, peppers, parsley, artichoke, Brussels sprouts, spinach, lemon, ginger, garlic, and red beets; those from dry fruits like apricots, prunes, and dates; from legumes including broad beans, pinto beans, and soybeans. Also nuts and seeds such as pecans, walnuts, hazelnuts, ground nut, and sunflower seeds; cereals such as barley, millet, oats, and corn. Many natural antioxidants are also available from a wide variety of spices including cloves, cinnamon, rosemary, and oregano. Less widely known sources of antioxidants include *Ginkgo biloba*, and tropical plants such as uyaku, and *Carica papaya*. Antioxidant properties of various teas and green tea, as well as fermented products such as red wine, have become of great interest in recent years and such would be suitable for use herein. Selenium is an excellent oxygen scavenger and works well, especially with vitamin or related tocopherol compounds. Synthetic dietary antioxidants include butylated hydroxyanisole (BHA) and butylated hydroxytoluene (BHT) which are commonly used in food products. Any of the foregoing, alone or in combination, are suited for use herein, as are combinations of natural and synthetic antioxidants. In one embodiment, the antioxidants comprise astaxanthin alone or in combination with other antioxidants.

The compositions comprise UFA and NORC, and B vitamins and antioxidants if included in the composition, in an amount effective for enhancing cognitive function. Generally, the compositions comprise from about 0.1% to about 50% UFA, and from about 0.1% to about 20% NORC. When included in the composition, the composition comprises from about 0.1 to 40 times the recommended daily requirement (RDA) of B vitamins and from about 0.0001% to about 25% of antioxidants. In various embodiments, the compositions comprise from about 1 to about 30% UFA, preferably from about 1 to about 15% UFA; and from about 1 to about 15% NORC, preferably from about 1 to about 10% NORC. In various embodiments, the B vitamins comprise from about 1 to 20 times the RDA, preferably from about 1 to 10 times the RDA, and antioxidants comprise from about 0.0001% to about 15%, most preferably from about 0.001% to about 5%, most preferably from about 0.001% to about 2%. In one embodiment, the compositions comprise UFA, NORC, and a mixture of one or more B vitamins and one or more antioxidants in such amounts. In one embodiment, the composition comprises from about 0.5 g to about 10 g UFA, and from about 0.5 g to about 10 g NORC, with or without the RDA for B vitamins and antioxidants.

The compositions may further comprise substances such as minerals, other vitamins, salts, functional additives including, for example, palatants, colorants, emulsifiers, antimicrobial or other preservatives. Minerals that may be useful in such compositions include, for example, calcium, phosphorous, potassium, sodium, iron, chloride, boron, copper, zinc, magnesium, manganese, iodine, selenium and the like. Examples of additional vitamins useful herein include such fat soluble vitamins as A, D, E, and K. Inulin, amino acids, enzymes, coenzymes, and the like may be useful to include in various embodiments.

In one embodiment, the compositions are food compositions, including human and pet food compositions. Such compositions include foods intended to supply the necessary dietary requirements for an animal, animal treats (e.g., biscuits), or dietary supplements. The compositions may be a dry composition (e.g., kibble), semi-moist composition, wet composition, or any mixture thereof. In another embodiment, the composition is a dietary supplement such as a gravy, drinking water, beverage, yogurt, powder, granule, paste, suspension, chew, morsel, treat, snack, pellet, pill, capsule, tablet, or any other suitable delivery form. The dietary supplement can comprise a high concentration of the UFA and NORC, and optional B vitamins and antioxidants. This permits the supplement to be administered to the animal in small amounts, or in the alternative, can be diluted before administration to an animal. The dietary supplement may require admixing, or preferably be admixed with water or other diluent prior to administration to the animal.

In one embodiment, the compositions are refrigerated or frozen compositions. In another embodiment, the UFA and NORC are pre-blended with the other components to provide the beneficial amounts needed. In yet other embodiments, the UFA and NORC are used to coat a food, snack, pet food composition, or pet treat. In one embodiment, the UFA and NORC are added to the composition just prior to offering it to the animal, e.g., using a sprinkled powder or a mix. Such compositions can further comprise B vitamins and/or antioxidants.

The compositions can optionally comprise one or more supplementary substances that promote or sustain general health. Preferred substances may be associated with improved mental health or enhanced cognitive function or may be substances that inhibit, delay, or decrease loss of cognitive function, e.g., herbs or plants that enhance cognitive function.

In various embodiments, pet food or pet treat compositions comprise from about 15% to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include pork, lamb, equine, poultry, fish, and mixtures thereof;

The compositions may further comprise from about 5% to about 40% fat. The compositions may further comprise a source of carbohydrate. The compositions may comprise from about 15% to about 60% carbohydrate. Examples of such carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products.

In some embodiments, the ash content of the composition ranges from less than 1% to about 15%, preferably from about 5% to about 10%.

The moisture content can vary depending on the nature of the composition. In a preferred embodiment, the composition is a complete and nutritionally balanced pet food. In this embodiment, the pet food may be a "wet food", "dry food", or food of intermediate moisture content. "Wet food" describes pet food that is typically sold in cans or foil bags, and has a moisture content typically in the range of about 70% to about 90%. "Dry food" describes pet food which is of a similar composition to wet food, but contains a limited moisture content, typically in the range of about 5% to about 15% or 20%, and therefore is presented, for example, as small biscuit-like kibbles. In one presently preferred embodiment, the compositions have moisture content from about 5% to about 20%. Dry food products include a variety of foods of various moisture contents, such that they are relatively shelf-stable and resistant to microbial or fungal deterioration or contamination. Also preferred are dry food compositions which are extruded food products, such as pet foods, or snack foods for either humans or companion animals.

The compositions may also comprise one or more fiber sources. The term "fiber" includes all sources of "bulk" in the food whether digestible or indigestible, soluble or insoluble, fermentable or nonfermentable. Preferred fibers are from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, *psyllium*, rice bran, carob bean gum, citrus pulp, fructooligosaccharide, pectin, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefit provided by the present disclosure to the immune system of an animal.

In other embodiments, the compositions further comprise prebiotics, probiotics, or a combination thereof. Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Prebiotics are non-digestible food ingredients that beneficially affect host health by selectively stimulating the growth and/or activity of bacteria in the colon. Prebiotics include fructooligosaccharides (FOS), xylooligosaccharides (XOS), galactooligosaccharides (GOS), and mannooligosaccharides (typically for non-human foods such as petfoods). The prebiotic, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of *bifidobacteria* in the colon, increasing calcium absorption, increasing fecal weight, shortening of gastrointestinal transit time, and possibly lowering blood lipid levels. The increase in *bifidobacteria* has been assumed to benefit human health by producing compounds to inhibit potential pathogens, by reducing blood ammonia levels, and by producing vitamins and digestive enzymes. Probiotic bacteria such as Lactobacilli or *Bifidobacteria* are believed to positively affect the immune response by improving the intestinal microbial balance leading to enhanced antibody production and phagocytic (devouring or killing) activity of white blood cells. *Bifidobacterium lactis* could be an effective probiotic dietary supplement for enhancing some aspects of cellular immunity in the elderly. Probiotics enhance systemic cellular immune responses and may be useful as a dietary supplement to boost natural immunity in otherwise healthy adults. Probiotics include many types of bacteria but generally are selected from four genera of bacteria: *Lactobacilllus acidophillus, Bifidobacteria, Lactococcus* and *Pediococcus*. Beneficial species include *Enterococcus* and *Saccharomyces* species. The amount of probiotics and prebiotics to be administered to the animal is determined by the skilled artisan based upon the type and nature of the prebiotic and probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, preferably from about 5 billion to about 10 billion live bacteria per day. Generally, prebiotics are administered in amounts sufficient to positively stimulate the healthy microflora in the gut and cause these "good" bacteria to reproduce. Typical amounts are from about one to about 10 grams per serving or from about 5% to about 40% of the recommended daily dietary fiber for an animal. The probiotics and prebiotics can be made part of the composition by any suitable means. Generally, the agents are mixed with the composition or applied to the surface of the composition, e.g., by sprinkling or spraying. When the agents are part of a kit, the agents can be admixed with other materials or in their own package.

The compositions and dietary supplements may be specially formulated for the intended recipients or consumers, such as for adult animals or for older or young animals. For example, a composition adapted for puppies or kittens or adapted for active, pregnant, lactating, or aging animals can be prepared. In general, specialized compositions will comprise energy and nutritional requirements appropriate for animals at different stages of development or age.

Certain aspects of the present disclosure are preferably used in combination with a complete and balanced food. According to certain embodiments provided herein, the compositions comprising the UFA and NORC, are preferably used with a high-quality commercial food. As used herein, "high-quality commercial food" refers to a diet manufactured to produce the digestibility of the key nutrients of 80% or more, as set forth in, for example, the recommendations of the National Research Council above for dogs, or in the guidelines set forth by the Association of American Feed Control Officials. Similar high nutrient standards would be used for other animals.

In one embodiment, the food compositions comprise any of a variety of ingredients or combinations thereof selected for their contributions to the overall composition. Thus a skilled food technologist may choose from among natural (e.g., plant or plant-derived, animal, or animal-derived, and microbial or microbially-derived), and synthetic ingredients or components. In particular embodiments, the ingredients may include any of the cereal grains and/or fractions or components thereof, meat and meat by-products, fish, shellfish, or other seafood, other animal products or by-products, eggs from any source, vitamins, minerals, salts, sweeteners, fiber, flavoring or other palatants, coloring, and functional ingredients such as emulsifiers, stabilizers, softeners, functional coatings, and the like. Cereals useful in the invention include all plants recognized as "cereal" crops, whether currently used in commercial agriculture or merely known practically or botanically as being a "cereal". For example, "cereals" includes corn, wheat, rice, barley, sorghum, millet, oats, rye, triticale, buckwheat, fonio, and *quinoa*. The skilled artisan will appreciate that in a given food composition, it is not uncommon to use one or more such cereal products. Meats useful in the composition include products from any animal, preferably muscle tissue such as chicken or other poultry, lamb, sheep, veal, beef, or pork. Other animal products and by-products useful in the composition include dairy products or by-products derived from the milk of any species. Other important components or ingredients include fats and the skilled artisan will appreciate that many sources of vegetable, animal, or microbial fats are available for formulating food compositions. In one embodiment, the source of fat is a plant fat such as corn, soy, or canola oil, preferably one that is readily available. In another embodiment, an animal fat, such as tallow, is useful for providing calories from fat, as well as enticing flavor to meat-eating animals. Of course, combinations of any of the foregoing ingredients, such as fats, are known in the art and useful for optimizing the food compositions based on functional properties as well as price and availability.

The skilled artisan will also appreciate that in formulating the food compositions of the present disclosure, the formulation may vary slightly, so as to allow consideration by the formulator of the price and/or availability of certain ingredients in the compositions, as well as the batch-to-batch variation in the analysis of certain ingredients. Thus a given food composition or formulation may vary slightly from batch to batch, plant to plant, or even season to season depending on such factors. Notwithstanding such variation in specific ingredients selected for manufacturing a particular batch of a food composition, the overall composition (for example, analysis of protein, carbohydrate, fat, fiber, or other component) may be held constant or at least substantially constant, for example, in accordance with a label claim, such as a claim or guarantee of a minimum or maximum percent of a particular component.

In other embodiments, the compositions of the present disclosure comprise UFA and NORC, and, if included in the composition, B vitamins and antioxidants in an amount effective for one or more of reducing or preventing a decline of social interaction, reducing or preventing age-related behavioral changes, increasing trainability, maintaining optimal brain function, facilitating learning and memory, reducing memory loss, retarding brain aging, preventing or treating strokes, preventing or treating dementia, and maintaining mental clarity and alertness in an animal.

The skilled artisan will understand how to determine the appropriate amount of UFA, NORC, B vitamins, antioxidants, and any other ingredients to be added to a given composition. The skilled formulator may consider important the animal's species, age, size, weight, health, and the like in determining how best to formulate a particular composition, food, or pharmaceutical composition comprising the UFA, NORC, and other components. Other factors that may be taken into account for formulation include the type of composition (e.g., pet food composition versus dietary supplement), the desired dosage of each component (UFA, NORC), the average consumption of specific types of compositions by different animals (e.g., based on species, body weight, activity/energy demands, and the like) and the manufacturing conditions under which the composition is prepared. Preferably, the concentrations of UFA and NORC to be added to the composition are calculated on the basis of the energy and nutrient requirements of the animal. When formulating the compositions of the present disclosure, a skilled can determine the amounts of the UFA, NORC, and other components of the compositions and of other compounds or ingredients, in for example a food composition, based upon the desired dosages and the characteristics of the animal.

For pet foods and food products formulated for human consumption, the amount of UFA as a percentage of the composition is preferably in the range of about 0.1% to about-13% of the composition, although a greater percentage can be supplied. In various embodiments, the amount of UFA is about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, or more e.g., 6%, 7%, 8%, 9%, 10%, 11%, 12%, 13%, 14%, 15%, 16%, 17%, 18%, 19%, 20% Or more Of the composition. Up to 30, 40, or 50% UFA may be used in certain embodiments.

For pet foods and food products formulated for human consumption, the amount of NORC as a percentage of the composition is in the range of about 0.1% to about 12% of the composition, although a greater percentage can be supplied. In various embodiments, the amount of NORC is about 0.1%, 0.2%, 0.3%, 0.4%, 0.5%, 0.6%, 0.7%, 0.8%, 0.9%, 1.0%, 1.1% 1.2%, 1.3%, 1.4%, 1.5%, 1.6%, 1.7%, 1.8%, 1.9%, 2.0%, 2.1%, 2.2%, 2.3%, 2.4%, 2.5%, 2.6% 2.7%, 2.8%, 2.9%, 3.0%, 3.1%, 3.2%, 3.3%, 3.4%, 3.5%, 3.6%, 3.7%, 3.8%, 3.9%, 4.0%, 4.1% 4.2%, 4.3%, 4.4%, 4.5%, 4.6%, 4.7%, 4.8%, 4.9%, 5.0%, Or more, e.g., 6%, 7%, 8%, 9%, 10%, 11%, 12% or more, up to about 15% or even 20% of the composition. In specific embodiments, 2-2.5% UFA and 2-2.5% NORC are used. In such embodiments, pure L-arginine is a preferred NORC compound. Dietary supplements may be formulated to contain several-fold higher concentrations of UFA and NORC, to be amenable for administration to an animal in the form of a tablet, capsule, liquid concentrate, emulsion, suspension, gel, or other dosage form, or to be diluted before administration, such as by dilution in water, or adding to a pet food (for example, by spraying or sprinkling thereon), and other modes of administration suitable for administering such dietary supplements.

In an alternative embodiment, the amount of UFA and NORC in the composition is a function of an amount required to establish specified concentrations, or a desired range of concentrations, of UFA and/or NORC, or a metabolite thereof, in the blood serum of the animal. The specified concentrations, or desired ranges of UFA and/or NORC in the blood serum may be calculated by determining the blood serum levels of animals fed the recommended amounts of UFA and NORC specified above, as would be appreciated by one of skill in the art.

In a preferred embodiment, the food compositions comprise a macronutrient composition suitable for the type of food being designed. In one embodiment, the food composition has about 20 to 32% protein, about 30 to 50% carbohydrate, about 5% to 20% fat, and about 15% to 25% moisture. In another embodiment, the food composition is a pet food composition such as a premium or super-premium pet food composition. In one embodiment, the pet food is formulated for canines and has a protein content of about 20-30%, preferably about 24-28%, and more preferably about 25-27%. In one embodiment, the protein content of a dog food composition is about 26% by weight. In another embodiment, the formulation is for felines and has a protein content of about 35-45%, preferably about 37-42%, and more preferably about 39-41%. In one embodiment, the protein content of a cat food composition is about 40%. In a preferred embodiment, the composition is a food product comprising UFA and NORC, and further comprising about 15% to about 50% protein, about 5% to about 40% fat, about 5% to about 10% ash content, and having a moisture content of about 5% to about 20%.

In one embodiment, the food composition is a wet food, such as a canned food, frozen food, or fresh food product. In one embodiment, the food composition is shelf stable. In another, it must be refrigerated. In other embodiments, the food composition is an intermediate moisture product or a dry food product as described above.

In a preferred embodiment, the UFA is a fish oil and the NORC is arginine or a nitric oxide-releasing derivative thereof. In certain embodiments, the compositions comprise from about 0.1% to about 50% fish oil and from about 0.1% to about 20% arginine. In preferred embodiments, both UFA and NORC are within the preferred ranges provided herein when the composition is a food product. Such ranges offer improved palatability and functional properties that will enhance acceptance of the food product.

In various embodiments, the composition is a human food composition, pet food composition, or a dietary supplement. The composition that is a dietary supplement may contain vastly different concentrations or amounts of the UFA and NORC than a food product or pet food. Generally, the palatability and similar sensory factors are not of concern with certain dietary supplements, e.g., those that are swallowed.

In one embodiment, the UFA comprises one or more of a natural fish oil, ALA, EPA, DPA, DHA, or another n-3 fatty acid from any source. Combinations of UFA sources are of course contemplated for use herein. UFA with n-3 or n-6 are also contemplated for use in various embodiments.

Preferably, the composition is formulated for a companion animal, e.g., a dog or cat. In other embodiments, the animal is a human, with or without an age-related cognitive decline.

In one embodiment, the composition is formulated to provide about 0.5 g to about 10 g each of UFA and NORC per day in one or more portions of a recommended serving size. For example, if the composition is intended for twice-per-day consumption, a 10 g dose can be provided by formulating the composition such that each recommended portion (e.g., 2 spoonful, or one 20 g portion, or the like) to provide 5 g each of UFA and NORC.

In a preferred embodiment, the compositions comprise from about 0.1% to about 50% fish oil; and from about 0.1% to about 20% arginine. Preferably, the compositions further comprise from about 0.1 to 40 times the recommended daily requirement of B vitamins, from about 0.0001% to about 25% antioxidants, or both. In one embodiment, the composition used in the methods comprises from about 0.5 g to about 10 g UFA, and from about 0.5 g to about 10 g NORC, with or without B vitamins and antioxidants.

In another aspect, the compositions further comprise one or more cognitive drugs in an amount effective for enhancing cognitive function. The skilled artisan can determine the amount of cognitive drug to be added to the composition based upon the recommended dosage for the drug given by its manufacturer or upon the animal's weight, species, age, health status, and the like.

In another aspect, the present disclosure provides pharmaceutical compositions comprising a composition of the present disclosure and one or more pharmaceutically-acceptable carriers, diluents, or excipients. Generally, pharmaceutical compositions are prepared by admixing a compound or composition with excipients, buffers, binders, plasticizers, colorants, diluents, compressing agents, lubricants, flavorants, moistening agents, and the like, including other ingredients known to skilled artisans to be useful for producing pharmaceuticals and formulating compositions that are suitable for administration to an animal as pharmaceuticals. Optionally, the pharmaceutical compositions further comprise one or both of a B vitamin and an antioxidant.

In another aspect, the present disclosure provides methods for enhancing cognitive function in an animal. The methods generally comprise administering to an animal a composition comprising one or more unsaturated fatty acids (UFA) and one or more nitric oxide releasing compounds (NORC) to the animal in an amount effective for enhancing cognitive function in the animal. In certain embodiments, the compositions further comprise one or more B vitamins, one or more antioxidants, or combinations thereof.

In some embodiments, the UFA, NORC, B vitamins, and antioxidants are administered to the animal in amounts given herein when describing the compositions. In one embodiment, the composition is administered in an amount effective to increase one or more cognitive, motor, or behavioral functions in animals, including animals of all ages that are healthy or animals that are susceptible to or suffering from a decline in cognitive function brought about by the aging process or by disease. In another embodiment, the composition is administered in an amount effective to prevent, reduce, or delay a decline in cognitive function in animals, particularly aging animals susceptible to or suffering from a decline in cognitive function brought about by the aging process or by disease. In certain embodiments, the daily dose for the compositions ranges from about 5 mg/day to about 5,000 mg/day, 10,000 mg/day, or 20,000, or more per animal. Preferably, the daily dose ranges from about 30 mg/day to about 10,000 mg/day per animal, and more preferably from about 750 mg/day to about 7,500 mg/day per animal. The daily dose of UFA and NORC can be measured in terms of grams of UFA and NORC per kg of body weight (BW) of the animal. The daily dose of UFA and NORC, therefore can range from about 0.001 g/kg to about 50 g/kg BW of the animal, although greater or lesser doses can be provided. Preferably, the daily dose of UFA and NORC is from about 0.001 g/kg to about 25 g/kg BW of the animal. More preferably, the daily dose of UFA and NORC is from about 0.001 g/kg to about 10 g/kg BW of the animal. More preferably, the daily dose of UFA and NORC is from about 0.001 g/kg to about 5 g/kg BW of the animal. More preferably, the daily dose of UFA and NORC is from about 0.001 g/kg to about 1 g/kg BW of the animal. More preferably, the daily dose of the UFA and NORC is from about 0.001 g/kg to about 0.5 g/kg BW of the animal.

In another aspect, the present disclosure provides methods for enhancing cognitive function in an animal. The methods generally comprise administering to an animal a composition comprising one or more unsaturated fatty acids (UFA) and one or more supplements that can be metabolized to produce nitric oxide releasing compounds (NORC) to the animal in an amount effective for enhancing cognitive function in the animal. In certain embodiments, the compositions further comprise one or more B vitamins, one or more antioxidants, or combinations thereof. The supplements are converted to NORC by the metabolic processes in the animals and the NORC are involved in enhancing cognitive function as described herein. In preferred embodiments, the supplements are citrulline/citrulline and ornithine. The supplements can be administered in any amount sufficient to obtain the NORC amounts required herein upon metabolism. Typically, the supplements are administered in a composition comprising UFA and supplements, preferably about 0.1% to about 50% UFA and 0.1% to about 20% supplement.

Only a portion of the arginine consumed by an individual remains available for metabolization to NO. Arginine is metabolized into citrulline and NO via the enzyme nitric oxide synthase (NOS). As much as 60% of ingested arginine is metabolized in the liver by arginase before entering the circulation, where any remaining arginine may be metabolized to citrulline and NO. An alternative source for arginine is the endogenous production of arginine from the amino acid citrulline. This route contributes about 20% to whole body arginine production. Citrulline is produced in the intestine and enters the circulation without being metabolized by the liver, with almost complete conversion to arginine in the kidneys. Citrulline passes through the liver with little or no metabolization and is converted to arginine in the mitochondria. The majority of circulating citrulline is converted in the kidneys, which are comprised of highly metabolically active tissue. Citrulline circulating in the bloodstream is first converted to arginine and then in cells to citrulline and NO. Citrulline can be administered via the gastrointestinal (GI) tract in oral and enteral products. Citrulline, endogenously, is a product of the metabolism of glutamine in the gut, generated from ornithine as part of the urea cycle, and formed by nitric oxide syntheses distributed in the body. Arginine is generated from citrulline, mainly in the kidney, through its metabolism by argininosuccinate synthase (EC 6.3.4.5) and argininosuccinate lyase (EC 4.3.2.1). Significantly, the conversion of citrulline to arginine occurs continuously, as long as citrulline is circulating in the bloodstream. As a result, circulating citrulline makes it possible to maintain elevated concentrations of arginine over time, which in turn makes it possible to maintain a steady release of NO in cells. Since the amino acid citrulline is a precursor to L-arginine, citrulline can substitute for L-arginine in nutritional compositions. Unlike arginine, citrulline is not metabolized by the liver following entry into the bloodstream through absorption from the diet or de novo intestinal production. Citrulline is enzymatically converted to arginine by mitochondria via a part of the urea cycle.

Similarly, ornithine is a precursor to L-arginine. As a result, ornithine can substitute for L-arginine in nutritional compositions. Unlike arginine, ornithine is not metabolized by the liver following entry into the bloodstream through absorption from the diet or de novo intestinal production. Ornithine is enzymatically converted to arginine by mitochondria via a part of the urea cycle.

Administration in accordance with the methods can be on an as-needed or as-desired basis of varying or regular frequency. A goal of regular ingestion is to provide the animal with a regular and consistent dose of the composition or the direct or indirect metabolites that result from such ingestion. Such regular and consistent dosing will tend to create constant blood levels of the components of the compositions or their direct or indirect metabolites. Thus, regular administration can be once monthly, once weekly, once daily, or more than once daily. Similarly, administration can be every other day, week, or month, every third day, week, or month, every fourth day, week, or month, and the like. Administration can be multiple times per day. When utilized as a supplement to ordinary dietetic requirements, the composition may be administered directly to the animal, e.g., orally, or otherwise. The compositions can alternatively be contacted with, or admixed with, daily feed or food, including a fluid, such as drinking water, or an intravenous connection for an animal that is receiving such treatment. When utilized as a daily feed or food, administration will be well known to those of ordinary skill.

Administration can also be carried out as part of a dietary regimen for the animal. For example, a dietary regimen may comprise causing the regular ingestion by the animal of a composition described herein in an amount effective to prevent, reduce, or delay a decline in one or more cognitive, motor, or behavioral functions in the animal.

According to the methods of the present disclosure, administration of the compositions, including administration as part of a dietary regimen, can span a period of time ranging from parturition through the adult life of the animal. In various embodiments, the animal is a human or companion animal such as a dog or cat. In certain embodiments, the animal is a young or growing animal. In more preferred embodiments, the animal is an aging animal. An animal that has reached about 35% of its projected lifespan is generally preferred. In presently preferred embodiments administration begins, for example, on a regular or extended regular basis, when the animal has reached more than about 30%, 40%, or 50% of its projected or anticipated lifespan. In some embodiments, the animal has attained 40, 45, or 50% of its anticipated lifespan. In yet other embodiments, the animal is older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

A composition or method for enhancing cognitive function has many effects on an animal. Many day-to-day life functions are dependent upon or related to cognitive function. For example, enhancing cognitive function is related to preventing a decline of social interaction, reducing or preventing age-related behavioral changes, increasing trainability, maintaining optimal brain function, facilitating learning and memory, reducing memory loss, retarding brain aging, preventing or treating strokes, and preventing or treating dementia in an animal. Similarly, enhancing cognitive function promotes the overall health and wellness of an animal. Further, enhancing cognitive function is integral to extending the prime for an animal. Therefore, enhancing cognitive function results in a benefit to the animal in one or more of these functions, e.g., an enhanced cognitive function allows the animal to interact more desirably with other animals, permits the animal to have a better memory, and counteract the affects of dementia. Basically, enhancing cognitive function results in an improvement in these and similar functions.

In various embodiments of the methods, the composition is a human food composition, pet food composition, or a dietary supplement. In other embodiments, the composition is a food composition further comprising about 15% to about 50% protein, about 5% to about 40% fat, about 5% to about 10% ash content, and having a moisture content of about 5% to about 20%.

In certain embodiments, the UFA is a fish oil and the NORC is arginine or a nitric oxide-releasing derivative thereof.

In certain embodiments, the composition being administered comprises from about 0.1% to about 50% fish oil and from about 0.1% to about 20% arginine. For embodiments of the methods, as with the compositions above, the UFA comprises one or more of a natural fish oil, ALA, EPA, DPA, DHA, another polyunsaturated fatty acid from any source, or combinations thereof.

In one embodiment, the composition used in the methods is formulated to provide about 0.5 g to about 10 g each of UFA and NORC per day via one or more portions of a recommended serving size. The composition can further comprise one or more B vitamins and one or more antioxidants. The B vitamin preferably comprises from about 0.1 to about 40 times the RDA and the antioxidant from about 0.0001% to about 25% of the composition. Preferably, the composition comprises a mixture of B vitamins.

In one embodiment, the composition is administered to the animal in conjunction with one or more cognitive drugs in an amount effective for enhancing cognitive and related functions as defined herein. In a particular embodiment, the composition administered is the pharmaceutical composition that includes a cognitive drug along with UFA and NORC. In a preferred embodiment, the composition is administered to the animal on a daily basis, preferably in a single dose.

In certain embodiments, the animal is a healthy aging animal. In others, the animal has a phenotype associated with age-related cognitive impairment. For example, when compared to a control animal not having the phenotype, the animal may have a phenotype that includes one or more of decreased ability to recall, short-term memory loss, decreased learning rate, decreased capacity for learning, decreased problem solving skills, decreased attention span, decreased motor performance, increased confusion, or dementia (Alzheimer's in humans or its equivalent in other animals).

In another aspect, the composition comprises UFA and NORC in an amount effective for improving one or more social behaviors. In a preferred embodiment, the animal is a companion animal.

The compositions, after being administered to an animal, are believed to increase the circulating concentrations of UFA and NORC in the blood or blood plasma of the animal. In certain embodiments, the blood concentration of a direct or indirect metabolite that results from the consumption of UFA and/or NORC is increased, and is useful as an indicator of dose. A decrease in concentration of one or more compounds in the bloodstream of an animal receiving the compositions can also occur in the normal course. Such decrease can also be a useful tool for monitoring or determining dosages. Preferably, the change in amount of the bloodstream component to be measured is dosage dependent. In some embodiments, the method results in an increase in one or more ketone bodies in the animal's blood. In embodiments where additional compounds are included in the compositions, e.g., B vitamins or antioxidants, administration results in an increase in circulating concentrations of these compounds and is useful as an indication of dose.

The present disclosure also provides other methods for affecting various cognitive, motor, or behavioral related functions and for affecting various physiological functions that relate to cognitive, motor, or behavioral functions, e.g., social interaction and brain aging. Generally, the methods comprise administering the compositions of the present disclosure to an animal in amounts defined herein for the compositions and methods.

In one aspect, the present disclosure provides methods for reducing or preventing a decline of social interaction in an animal comprising administering a composition comprising UFA and NORC to the animal in an amount effective to reduce or prevent a decline in social interaction. In preferred embodiments, the compositions further comprise one or more B vitamins, one or more antioxidants, or both in amounts effective for reducing or preventing a decline of social interaction in an animal. The methods ensure that an aging animal remains involved in playtime, participates in group activities, interacts with caregivers, and the like.

In one aspect, the present disclosure provides methods for reducing or preventing a decline of social interaction in an animal comprising administering a composition comprising UFA and NORC to the animal in an amount effective to reduce or prevent a decline in social interaction. In preferred embodiments, the compositions further comprise one or more B vitamins, one or more antioxidants, or both in amounts effective for reducing or preventing a decline of social interaction in an animal. The methods ensure that an aging animal remains involved in playtime, participates in group activities, interacts with caregivers, and the like.

In another aspect, the present disclosure provides methods for reducing or preventing age-related behavioral changes in an animal comprising administering UFA and NORC to the animal in an amount effective for reducing or preventing age-related behavioral changes in the animal. Preferably, the age-related behavioral changes are one or more of forgetfulness, disorientation, reduced social interaction, changes in sleep and wake habits (particularly an increase in nighttime activity), loss of "housetraining" that results in changes in urination and defecation locations and patterns, confusion, frustration, change in temperament such as agitation and aggression, pacing, and wandering. Such changes have been noted in response to cognitive declines in humans and other animals. In preferred embodiments, the compositions further comprise one or more B vitamins, one or more antioxidants, or both in amounts effective for reducing or preventing age-related behavioral changes in an animal.

In another aspect, the present disclosure provides methods for increasing trainability of an animal comprising administering a composition comprising UFA and NORC to the animal in an amount effective for increasing trainability. For example, administering the composition while "potty training" babies, puppies, and kittens permits the animal to learn the task more quickly than if the training occurred without using the composition. Similarly, training a dog or cat to obey verbal, signal, or other commands permits the animal to learn the task more quickly than if the training occurred without using the composition. Similarly, the compositions could be useful for training feral or wild animals such as animals used in a circus or pets raised in the wild. In preferred embodiments, the compositions further comprise one or more B vitamins, one or more antioxidants, or both in amounts effective for increasing trainability of an animal.

In another aspect, the present disclosure provides methods for maintaining optimal brain function in an animal. The methods comprise administering a composition comprising UFA and NORC to the animal in an amount effective to prevent or delay a decline in brain function, particularly over time. In preferred embodiments, the compositions further comprise one or more B vitamins, one or more antioxidants, or both in amounts effective for maintaining optimal brain function in an animal. Generally, the methods ensure that an aging animal maintains healthy and optimal brain function throughout life and has a better quality of life, particularly in older animals. The methods also slow the progression of mental decline in aging dogs.

In another aspect, the present disclosure provides methods for facilitating learning and memory in an animal. The methods comprise administering a composition comprising UFA and NORC to the animal in an amount effective for facilitating learning and memory in the animal. In one embodiment, the animal has reached at least about 50% of its life expectancy. The methods help an aging animal remember facts and understand instructions. In preferred embodiments, the compositions further comprise one or more B vitamins, one or more antioxidants, or both in amounts effective for facilitating learning and memory in an animal.

In another aspect, the present disclosure provides methods for reducing memory loss in an animal. The methods comprise administering a composition comprising UFA and NORC to the animal in an amount effective to reduce memory loss over time. In preferred embodiments, the compositions further comprise one or more B vitamins, one or more antioxidants, or both in amounts effective for reducing memory loss in an animal.

In another aspect, the present disclosure provides methods for retarding brain aging in an animal. The methods comprise administering a composition comprising UFA and NORC to the animal in an amount effective to retard brain aging. In preferred embodiments, the compositions further comprise one or more B vitamins, one or more antioxidants, or both in amounts effective for retarding brain aging in an animal.

In another aspect, the present disclosure provides methods for preventing or treating strokes in an animal. The methods comprise administering a composition comprising UFA and NORC to the animal in an amount effective to prevent or treat strokes. In preferred embodiments, the compositions further comprise one or more B vitamins, one or more antioxidants, or both in amounts effective for preventing or treating strokes in an animal. The methods are based upon the discovery that reducing damage that results from strokes is correlated to certain aspects of enhancing cognitive function, e.g., reducing memory loss.

In another aspect, the present disclosure provides methods for preventing or treating dementia in an animal. The methods comprise administering a composition comprising UFA and NORC to the animal in an amount effective to prevent or treat dementia. In preferred embodiments, the compositions further comprise one or more B vitamins, one or more antioxidants, or both in amounts effective for preventing or treating dementia in an animal. Dementia can be Alzheimer's disease (AD) in humans, Canine Cognitive Dysfunction Syndrome (CCDS) in canines, or similar diseases in other animals. The methods are based upon the discovery that the compositions and methods of the present disclosure prevent or reduce dementia by reducing the effects of damage that results from the causes of dementia, e.g., amyloid deposits or deterioration of artery function.

In another aspect, the present disclosure provides methods for maintaining mental clarity and alertness in an animal. The methods comprise administering a composition comprising UFA and NORC to the animal in an amount effective for maintaining mental clarity and alertness. In preferred embodiments, the compositions further comprise one or more B vitamins, one or more antioxidants, or both in amounts effective for maintaining mental clarity and alertness in an animal.

In one aspect, the present disclosure provides methods for promoting the health and wellness of an animal comprising administering a composition comprising UFA and NORC to the animal in an amount effective to promote health and wellness. In preferred embodiments, the compositions further comprise one or more B vitamins, one or more antioxidants, or both in amounts effective for promoting health and wellness.

In a further aspect, the present disclosure provides methods for extending the prime for an animal comprising administering a composition comprising UFA and NORC to the animal in an amount effective for extending the prime for the animal. In preferred embodiments, the compositions further comprise one or more B vitamins, one or more antioxidants, or both in amounts effective for extending the prime for the animal.

In the methods for reducing or preventing a decline of social interaction, reducing or preventing age-related behavioral changes, increasing trainability, maintaining optimal brain function, facilitating learning and memory, reducing memory loss, retarding brain aging, preventing or treating strokes, preventing or treating dementia, maintaining mental clarity and alertness, promoting health and wellness, and extending the prime, the animal is preferably a human or companion animal, most preferably a dog or cat. The amounts of UFAs, NORC, B vitamins, antioxidants, and other ingredients used in these methods are the same as the amounts or within the ranges given for enhancing cognitive function.

In a further aspect, the present disclosure provides kits suitable for administering a composition comprising one or more UFA and NORC to an animal. The kits comprise in separate containers in a single package or in separate containers in a virtual package, as appropriate for the kit component, (a) one or more UFAs, (b) one or more NORC, and one or more of (1) one or more other ingredients suitable for consumption by an animal; (2) one or more B vitamins; (3) one or more antioxidants; (4) one or more cognitive drugs; (5) one or more prebiotics; (6) one or more probiotics; (7) one or more diagnostic devices suitable for determining whether an animal could benefit from compositions and methods for enhancing cognitive function and related functions; (8) instructions for how to combine or prepare the UFA and NORC and any other ingredients provided in the kit for administration to an animal; (9) instructions for how to use the combined kit components, prepared kit components, or other kit components for-the benefit of an animal; and (10) a device for administering the combined or prepared kit components to an animal. The components are each provided in separate containers in a single package or in mixtures of various components in different packages. In preferred embodiments, the kits comprise the UFAs, NORC, B vitamins, and antioxidants. The kits may comprise the ingredients in various combinations. For example, the kit could comprise a mixture of one or more B vitamins and one or more antioxidants in one container and one or more other ingredients in one or more other containers. Similarly, the kit could comprise a mixture of UFA and NORC in one container and one or more other ingredients in one or more other containers. Other such combinations can be produced by the skilled artisan based upon the characteristics of the ingredients and their physical and chemical properties and compatibilities.

In another aspect, the present disclosure provides a means for communicating information about or instructions for one or more of (1) using compositions of the present disclosure for enhancing cognitive function; (2) admixing the UFAs, NORC, B vitamins, antioxidants, or other components of the present disclosure to produce a composition suitable for enhancing cognitive function; (3) using the kits of the present disclosure for enhancing cognitive function; and (4) administering the compositions to an animal. The means comprises one or more of a physical or electronic document, digital storage media, optical storage media, audio presentation, audiovisual display, or visual display containing the information or instructions. Preferably, the means is selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In another aspect, the present disclosure provides methods for manufacturing a food composition comprising UFA, NORC, and one or more other ingredients suitable for consumption by an animal, e.g., protein, fat, carbohydrate, fiber, B vitamins, and antioxidants. The methods comprise admixing one or more ingredients suitable for consumption by an animal with UFA and NORC, and possibly other ingredients such as B vitamins and/or antioxidants. Alternatively, the methods comprise applying UFA and NORC, and other ingredients if desired, separately or in any combination onto the food composition, e.g., as a coating or topping. The UFA and NORC can be added at any time during the manufacture and/or processing of the food composition. This includes, for example, admixing the UFA and NORC as part of the core formulation of the "body" of the food composition or applying them as a coating, i.e., primarily to the surface of the food composition after its manufacture. The compositions can be made according to any method suitable in the art.

In another aspect, the present disclosure provides a package comprising a composition of the present disclosure and a label affixed to the package containing a word or words, picture, design, acronym, slogan, phrase, or other device, or combination thereof, that indicates that the contents of the package contains a composition suitable for enhancing cognitive function, reducing or preventing a decline of social interaction, reducing or preventing age-related behavioral changes, increasing trainability, maintaining optimal brain function, facilitating learning and memory, reducing memory loss, retarding brain aging, preventing or treating strokes, preventing or treating dementia, or maintaining mental clarity and alertness in an animal, particularly an aging animal. Typically, such device comprises the words "improves cognitive function", "improves memory", "reduces memory loss in aging animals", "maintains mental clarity and alertness" or an equivalent expression printed on the package. Any package or packaging material suitable for containing the composition is useful in the present disclosure, e.g., a bag, box, bottle, can, pouch, and the like manufactured from paper, plastic, foil, metal, and the like. In a preferred embodiment, the package contains a food composition adapted for a particular animal such as a human, canine or feline, as appropriate for the label, preferably a companion animal food composition.

In another aspect, the present disclosure provides for use of UFA and NORC to prepare a medicament for enhancing cognitive function, reducing or preventing a decline of social interaction, reducing or preventing age-related behavioral changes, increasing trainability, maintaining optimal brain function, facilitating learning and memory, reducing memory loss, retarding brain aging, preventing or treating strokes, preventing or treating dementia, and maintaining mental clarity and alertness in an animal. The medicament can further comprise one or more B vitamins, antioxidants, or combinations thereof. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

In the present disclosure, the animal can be a juvenile, adult, senior, or geriatric animal. Typically, for most embodiments, the animal is an aging animal. Generally, animals are senior in the last half of their expected lifespan and geriatric in the last fourth of their expected lifespan. Lifespan definitions vary for various animals and are known to skilled artisans. For example, an animal is considered to be juvenile until about 16 years of age. For a dog or cat, the animal is considered to be juvenile until 1 year of age.

The compositions of the present disclosure, including the pharmaceutical compositions and medicaments, are administered to the animal using a variety of administration routes. Such routes include oral, intranasal, intravenous, intramuscular, intragastric, transpyloric, subcutaneous, rectal, and the like. Preferably, the compositions are administered orally.

The compositions of the present disclosure, including the pharmaceutical compositions and medicaments, are administered to the animal for a time required to accomplish one or more objectives of the present disclosure, e.g., enhancing cognitive function, reducing or preventing a decline of social interaction, reducing or preventing age-related behavioral changes, increasing trainability, maintaining optimal brain function, facilitating learning and memory, reducing memory loss, retarding brain aging, preventing or treating strokes, preventing or treating dementia, and maintaining mental clarity and alertness in an animal. The compositions are suitable for long-term administration or administration on any schedule compatible with the composition and objective.

In various embodiments of the methods and compositions of the present disclosure, the antioxidants comprise astaxanthin alone or in combination with other antioxidants.

EXAMPLES

The present disclosure can be further illustrated by the following examples, although it will be understood that the examples are included merely for purposes of illustration and are not intended to limit the scope of the present disclosure unless otherwise specifically indicated.

Example 1

Animal and Test Groups

Cognitively-experienced beagle dogs (males and females ranging from 7.5 to 11.6 years of age) were tested. The average age of the dogs was 9.38 years. To qualify, the dogs must have had at least 6 months of previous cognitive test experience, including having been trained on the delayed non-matching-to position task (DNMP) and the oddity task.

During an initial baseline phase, all dogs were tested on a variable delay version of the DNMP task (or at 5 s if previously unable to learn the task) that provided a means of assessing visuo-spatial working memory and on a size discrimination and reversal task. Performance on these tasks was used to place the dogs into four cognitively equivalent treatment groups (twelve dogs per group): (1) 2% fish oil, 2.5% arginine, 1 to 40 times RDA B vitamins, 150 mg/kg vitamin C, 900 mg/kg vitamin E, and 0.5 mg/kg selenium ("SPB Group"); and (2) the Control Group.

Feeding and Water

Dogs had free access to water via wall-mounted automatic watering systems and/or water bowls. The animals were provided one of five adult maintenance foods having approximately 32% protein, 20% fat, and 3% fiber once daily. Initial individual food amounts were calculated using the formula "kcal requirement=110 kcal/day×(BW×0.75)", where BW is body weight. The formula was intended to maintain a constant body weight at an appropriate body condition.

Dogs were weighed weekly at the start of treatment and twice monthly after food intake and body condition stabilization; food intake was adjusted as needed to maintain a relatively constant body weight. Animals were given approximately 30 minutes to eat the food provided. The approximate amount of food remaining was recorded in a food intake monitoring datasheet for each animal.

Housing Conditions

Cognitive Test Battery

Landmark discrimination learning (Days 7-99). Egocentric learning and reversal (Days 100-163).

Landmark Discrimination Task

In this task, the dogs were trained to approach one of two objects, based on their proximity to an external landmark. The task was intended to assess allocentric spatial ability, which entails utilization of external landmarks to localize objects in space. The dogs were tested on successively more difficult versions of the same general problem.

General test procedures: Dogs were subject to ten (10) trials per day, with an inter-trial interval of 30 seconds. Testing was conducted once per day, approximately six days per week, such that a total of 80 sessions were conducted. A partial correction procedure was used. In this procedure, once each session the dogs are permitted to correct their response after making an error. Each dog was tested on up to four problems, depending upon the dog's success at solving the problems. To move on from the first and second problems, the dog had to complete a two-stage criterion. To pass the first stage, the dog had to respond correctly in at least 9 of 10 trials, or on 8 of 10 trials over 2 consecutive days. Dogs had to respond in all trials to pass the first stage. The second criterion stage was completed when the dog responded correctly in at least 70% of the next 30 trials over three consecutive sessions. Dogs that had a non-response in any one trial were assigned a score of 0.5, which was assumed to be the response based on random choice, and were given one extra day of testing to complete the 30 trials. An average score of 70% over all test days was required to pass the second stage.

The discriminada were identical white coasters and a yellow wooden peg, 2 cm×2 cm×9 cm, which served as the landmark. The white circular coasters were placed over the two lateral food wells on the presentation tray. Velcro tabs 2 cm in diameter, to hold the landmark in place, were glued to the top center of the coasters and to appropriate loci on the food tray.

Initial Landmark Test (Land-0): On the initial test (L0), the landmark was attached to the center of one of the two white coasters. On each trial, the experimenter placed the food reward in either the left or right food well and positioned the landmark accordingly. The door was raised and the tray was moved to approximately 25 cm from the dog for a brief inspection interval to enable the dog to see the spatial arrangement on the tray. The tray was then presented to the dog and the dog was allowed to respond. In this and all subsequent levels, the dogs were required to respond to the coaster closest to the landmark to obtain the food reward. The correct side was determined randomly by the computer with the constraint that each side was correct on half of the trials of each test session. Each dog was allowed a maximum of 30 test sessions (300 trials) to learn to respond to stimulus associated with the landmark during L0.

Remedial Training: Dogs that failed the initial L0 test were given a remedial training program to help teach them the task. The remedial training consisted of 5 additional training days, with 15 trials per day. At the start of the remedial training, the animals were presented with a single rewarded stimulus on the majority of the trials. With continued testing, additional paired stimulus presentations were given. After completing the remedial learning phase, the animals received additional training, up to a maximum of 10 sessions using the original protocol. This protocol was also used for dogs that failed L1. Dogs that failed L0 were moved on to Li. Dogs that failed remedial training after Li were moved on to the next task, if 80 test sessions had not elapsed. If fewer that 10 test sessions remained, the animals on L1 received extra remedial training sessions.

Landmark-1 (L1): Once a dog learned the L0 task (either during the initial training or after the remedial training), the landmark was moved 1 cm medially and diagonally away from the edge of the coaster, which constituted landmark 1 (L1). The landmark was attached to the food tray with a black piece of 2 cm wide Velcro. Dogs that did not learn within 30 sessions were given remedial training, as described above for LO.

Egocentric Test Protocol.

General Test Procedure: At the start of a trial the hinged door was opened to present the stimulus tray to the dog and the dog was allowed a maximum of 30-sec to make a response by displacing one of the two identical stimuli. A correct response was counted when the dog displaced a stimulus object covering food reward. An error was counted when the dog displaced the non-rewarded stimulus. The animals received 12 trials per session over a period of 63 sessions.

Preference Phase: On the first test day the dogs were given a preference test consisting of 10 discrete trials with objects covering both lateral food wells to determine if any side preferences were present. The preferred side was used as the positive side for the initial acquisition phase of testing. Thus, if the animal chose the object to it's left most frequently, then the animals' left side was designated its preferred side. For animals that did not show a side preference (and responded five times to each side), a coin toss was used to determine the rewarded side.

Acquisition Phase: Each trial consisted of a single presentation of the stimulus tray with a stimulus covering a reward in the preferred side lateral well, or the center well. A second non-rewarded stimulus object covered a well towards the dog's non-preferred side. Consequently, the object furthest to the animals' preferred side was always rewarded. On any given trial, there were three possible spatial configurations (left-center, left, right, or right-center). Each configuration occurred four times per test session.

Criterion: The acquisition phase was successfully completed once a dog scored a minimum of 90% correct (33/36 correct trials) over three consecutive test sessions. A maximum of 12 sessions, or 144 trials, were given to meet this criterion. Animals that did not learn within 12 sessions were given 5 sessions of remedial training, which was followed by up to 10 additional sessions.

Reversal Phase: Once an animal passed the acquisition phase, the rewarded position was switched to the opposite side. Thus, if the object closest to a dog's right was rewarded in acquisition testing, the object closest to its left was rewarded in the reversal testing. For the first reversal test, the learning criterion was the same as for the original acquisition. A maximum of 15 sessions, or 180 trials, were given to meet this criterion. If an animal did not satisfy the criterion within 15 sessions, 5 sessions of remedial training were given. The animals then received 10 additional sessions to reach the learning criterion.

Repeated (Multiple) Reversal Phase: Once an animal learned the original reversal, the correct side was then be switched and the animal retested until it relearned the task. This procedure was repeated until the animals had completed a total of 52 sessions on the egocentric protocol. The results are shown in Tables 1 to 5.

Landmark Test Results

TABLE 1

Landmark-0 test results

| Test Group | Errors to Criterion Means | SE |
|---|---|---|
| Control | 45.42 | 12.85 |
| SPB | 29.38 | 8.10 |

Referring to the data, the SPB Group performed better than the Control Group.

TABLE 2

Landmark-1 test results

| Test Group | Errors to Criterion Means | SE |
|---|---|---|
| Control | 136.96 | 16.26 |
| SPB | 89.29 | 19.03 |

The Control Group differed significantly from the SPB Group.

Egocentric Test Results

TABLE 3

Acquisition test results

| Test Group | Errors to Criterion Means | SE |
|---|---|---|
| Control | 25.58 | 2.96 |
| SPB | 20.41 | 2.71 |

Referring to the data, the Control Group differed from the SPB group.

TABLE 4

Reversal test results

| Test Group | Errors to Criterion Means | SE |
|---|---|---|
| Control | 68.29 | 6.22 |
| SPB | 47.09 | 5.58 |

Referring to the data, the Control Group differed significantly from the SPB Group.

TABLE 5

Repeated reversal test results

| Test Group | Errors to Criterion Means | SE |
|---|---|---|
| Control | 2.4 | 0.40 |
| SPB | 4.42 | 0.48 |

Example 2

Male Charles Rivers Sprague-Dawley rats (250 g, Wilmington, Mass.) were acclimatized to animal facilities 3 days prior to surgery with a 12 hour light-dark cycle. Bilateral ovariectomy was performed 2 weeks before diet feeding began. Four weeks after the start of diet feeding, transient middle cerebral artery (tMCA) occlusion under anesthesia was performed following intraperitoneal injection of ketamine (60 mg/kg) and xylazine (10 mg/kg). 15 rats per group were randomly assigned to one of four treatment groups:

Group 1—Neutered+Control Diet
Group 2—Neutered+Diet II
Group 3—Intact+Control Diet
Group 4—Intact+Diet II The Control Diet was a standard rat diet containing 140 g/kg casein, 100 g/kg sucrose, 50 g/kg fiber, 155 g/kg dextrin, 466 g/kg corn starch, 35 g/kg standard salt mix, 40 g/kg soybean oil, 10 g/kg standard vitamin mix, 1.8 g/kg L-cysteine and 2.5 g/kg choline chloride. Diet II was the Control Diet plus 2% Arginine, 2% Menhaden fish oil 4× B vitamins, and antioxidants (Vitamin E: 500 mg/kg diet, Vitamin C: 150 mg/kg diet, Astaxanthin: 100 mg/kg, selenium: 0.40 mg/kg).

Animals were anesthetized by an intraperitoneal injection of ketamine (60 mg/kg) and xylazine (10 mg/kg). tMCA occlusion was performed as previously described (Simpkins et al., 1997) with slight modification. Briefly, the left common carotid artery, external carotid artery and internal carotid artery were exposed through a midline cervical incision. A 3.0 mono-filament suture was introduced into the internal carotid artery lumen and gently advanced until resistance was felt. The surgical procedure was performed within 20 minutes, with minimal bleeding. The suture was kept in place for 60 minutes and then withdrawn to allow reperfusion. Rectal temperature was monitored and maintained between 36.5 and 37° C. with a heating pad throughout the procedure. At 24 hours after the onset of reperfusion, the animals were sacrificed and the brains were removed. The brains were then dissected coronally into 2 mm sections using a metallic brain matrix (AS1 Instruments Inc.; Warren, Mich.) and stained by incubation in a 2% solution of 2,3,5-triphenyltetrazolium chloride (TTC) in physiological saline at 370 C, and then fixed in 10% formalin. DNA fragmentation analysis with TdT-mediated dUTP Nick-End Labeling (TUNEL) MCA occlusion is a widely used focal ischemic stroke model (Bederson et al., 1986). This in vivo model for neuronal death can rapidly induce a synchronized apoptotic process in a large number of neurons and other cells (Li et al., 1997). The effects of transient ischemia on apoptosis were therefore examined by analyzing DNA fragmentation with the TUNEL assay. TUNEL staining was performed according to the modified manufacturer's instructions (Gavrieli et al., 1992). Formalin-fixed, paraffin-embedded tissue sections were deparaffinized with xylene, rehydrated through graded ethanol treatment, and given a final wash in PBS. The sections were post-fixed in 4% paraformaldehyde for 20 minutes. Sections were then washed and treated for 15 minutes with 100/pg/ml proteinase K in PBS, equilibrated with equilibration buffer for 10 min, and then incubated with buffer containing TdT enzyme and FITC-labeled dUTP (Promega, Madison, Wis.) at 370 C in a humidified chamber. The reaction was terminated by incubation in 2×SSC buffer for 15 min at room temperature. The sections were then mounted with anti-fade reagents containing DAPI (Molecular Probes, Eugene, Oreg.). Positive control sections were immersed in DNase I solution for 10 min at room temperature before equilibration in TdT buffer. The sections were observed under a fluorescent microscope with appropriate excitation/emission filter pairs.

After the surgery, some animals died before the necropsy. The number of animals quantified for lesion volume ranged from 12 to 15 per group. The results are shown in Tables 6 and 7.

The results were analyzed with one-way analysis of variance (ANOVA) using Prism software (Graphpad Inc; San Diego, Calif.). The significance of differences among groups was determined by one-way ANOVA followed by Tukey's multiple comparison tests. All values were expressed as mean±SEM.

Referring to Tables 6 and 7, the results show that a diet containing one or more of the ingredients given in Diet II has a beneficial effect on preventing or treating ischemia and as such a beneficial effect on many brain related functions, e.g., cognitive function, social interaction, age-related behavioral changes, decline in brain function, enhancing brain functions, preventing or treating strokes, retarding brain aging, and preventing or treating dementia such as Alzheimer's disease.

TABLE 6

The Effect of Diet II on the Lesion Volume (mm3) Induced by Transient Focal Cerebral Ischemia

|  | Control + Castration | Diet II + Castration* | Intact + Control | Intact + Diet II |
|---|---|---|---|---|
| n | 13 | 12 | 14 | 14 |
| Mean | 284.9 | 133.6 | 244.5 | 163.1 |
| Std. Error | 32.50 | 28.53 | 43.30 | 31.54 |

*p < 0.05 Diet II + Castration vs Control + Castration

TABLE 7

The Effect of Diet II on the Apoptotic Index (%) Induced by Cerebral Ischemia

|  | Control + Castration | Diet II + Castration* | Intact + Control | Intact + Diet II |
|---|---|---|---|---|
| n | 13 | 12 | 14 | 14 |
| Mean | 85.55 | 46.67 | 75.15 | 57.69 |
| Std. Error | 4.134 | 7.51 | 8.208 | 8.137 |

Example 3

This example provides data from experiments on several neural cell models that show the synergistic effect of an NO-releasing compound and a PUFA (e.g., DHA). For a neuronal model, human iCell neurons (Cellular Dynamics International) were plated in 96-well plates and were grown to neuronal maturity by culturing for 2 weeks. For a co-culture model, human iCell astrocytes and iCell neurons (Cellular Dynamics International) were plated in 96-well plates and were grown to neural maturity for 2 weeks.

In each model, cells were then treated with DHA (UFA), arginine and citrulline (NORC's) at 3 different concentrations (see table 1 in FIG. 1) for 2 days. The supernatant was used to perform Amyloid beta 42 (Aβ1-42) ELISA Kit, Human (KHB3441, Thermo Fisher Scientific). N=6; One-way ANOVA with Tukey's multiple comparison test, *p<0.05; p<0.01; *p<0.001. The results obtained are shown in FIG. 2 and FIG. 3.

The release of Aβ1-42 is significantly decreased for the DHA+NORC blend compared to DHA alone or NORC alone. To this end, it is important to note that it is known for instance that Aβ1-42 is a major component of cerebrovascular amyloid deposits and hence this has implications for the pathology of cognitive decline caused by damage from disease such as Alzheimer's disease.

In the left panel of FIG. 2, the combination of UFA+NORC (DHA+arginine) is shown to be significantly different than for the controls (UFA and NORC alone). As shown in the right panel of FIG. 2, citrulline alone has no effect, nor DHA, but there is a significant decrease for the blend of UFA+NORC (DHA+citrulline).

Figure 3:
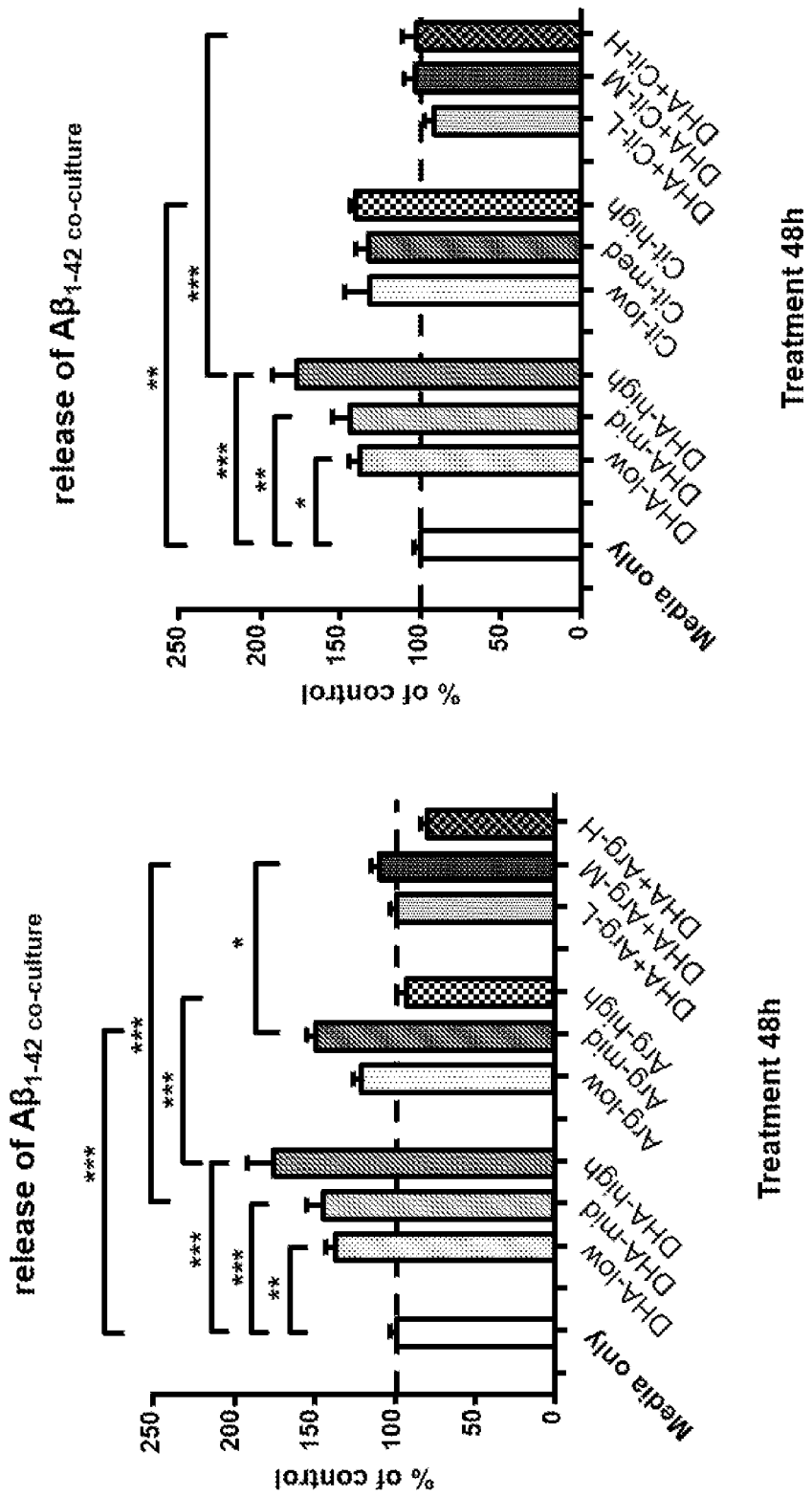
FIG. 3 contains graphs depicting results regarding co-cultures from the experimental study disclosed herein as Example 3.

FIG. 3 shows that the composition of UFA+NORC is significantly different than for the controls (NORC and UFA alone) in the Aβ 1-42 test in co-culture.

In view of these experimental results, the observed synergistic effect of a combination of UFA and NORC on neural human cell models when compared to the control group, provides evidence for the effect of such combination on the pathology of cognitive decline caused by damage from disease or changes in brain function upon administration of a composition comprising UFA and NORC.

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims the invention may be practiced otherwise than as specifically described.

The invention is claimed as follows:

1. A method for enhancing cognitive function in an aging companion animal, the method comprising:
    identifying an aging companion animal in which enhancement of cognitive function is desired; and
    administering a composition comprising effective amounts of arginine and docosahexaenoic acid (DHA) to the aging companion animal on a daily basis, wherein the composition is administered in a daily dose comprising about 0.001 g to about 50 g of the DHA/kg body weight of the aging companion animal and about 0.001 g to about 50 g of the arginine/kg body weight of the aging companion animal, the administration on a daily basis of the composition for a time period results in enhanced cognitive function in the aging companion animal compared with an equivalent aging companion animal not administered the composition for an equivalent time period, the DHA is about 1% to about 15% of the composition, and the arginine is about 0.1% to about 20% of the composition.

2. The method of claim 1 wherein the composition further comprises one or more of a natural fish oil, alpha-linolenic acid (ALA), eicosapentaenoic acid (EPA), docosapentaenoic acid (DPA), or another n-3 fatty acid from any source.

3. The method of claim 1 wherein the time period is at least one month.

4. The method of claim 1 wherein the composition is a complete and nutritionally balanced pet food.

5. The method of claim 1 wherein the daily dose of the composition comprises about 0.001 g of the DHA/kg body weight of the aging companion animal to about 1.0 g of the DHA/kg body weight of the aging companion animal per day.

6. The method of claim 1 wherein the daily dose of the composition comprises about 0.001 g of the DHA/kg body weight of the aging companion animal to about 0.5 g of the DHA/kg body weight of the aging companion animal per day.

7. The method of claim 1 wherein the daily dose of the composition comprises about 0.001 g of the arginine/kg body weight of the aging companion animal to about 1.0 g of the arginine/kg body weight of the aging companion animal per day.

8. The method of claim 1 wherein the daily dose of the composition comprises about 0.001 g of the arginine/kg body weight of the aging companion animal to about 0.5 g of the arginine/kg body weight of the aging companion animal per day.

9. The method of claim 1 wherein the aging companion animal is a healthy aging companion animal, and the administration of the DHA and the arginine results in enhanced cognitive function in the healthy aging companion animal relative to an equivalent healthy aging companion animal not administered the DHA and the arginine.

10. The method of claim 1 wherein the aging companion animal has a phenotype associated with age related cognitive impairment, and the administration of the DHA and the arginine results in enhanced cognitive function in the aging companion animal relative to an equivalent aging companion animal having the phenotype associated with age-related cognitive impairment and not administered the DHA and the arginine.

11. The method of claim 10 wherein the phenotype includes one or more of decreased ability to recall, short-term memory loss, decreased learning rate, decreased capacity for learning, decreased problem solving skills, decreased attention span, decreased motor performance, increased confusion, or dementia, as compared to a control aging companion animal not having the phenotype.

12. The method of claim 10 wherein the phenotype comprises dementia.

13. The method of claim 1 wherein the composition comprises from 0.1 to 40 times the recommended daily requirement of B vitamins.

14. The method of claim 1 wherein the composition comprises about 0.0001% to about 25% of antioxidants.

15. The method of claim 1, wherein the aging companion animal is a dog that has Canine Cognitive Dysfunction Syndrome (CCDS).

16. The method of claim 1, wherein the composition consists essentially of (i) unsaturated fatty acids comprising the DHA, (ii) one or more nitric oxide releasing compounds comprising the arginine, (iii) optionally B vitamins and (iii) optionally one or more antioxidants.

17. The method of claim 1, wherein the composition is a pet food or pet treat and comprises from about 15 wt. % to about 50 wt. % crude protein, about 5 wt. % to about 40 wt. % fat, about 15 wt. % to about 60 wt. % carbohydrate, an ash content no greater than about 15 wt. %, and a moisture content from about 5 wt. % to about 20 wt. %.

18. The method of claim 1, wherein the aging companion animal is a canine, and the composition has a protein content of about 20 wt. % to 30 wt. %.

19. The method of claim 1, wherein the aging companion animal is a feline, and the composition has a protein content of about 35 wt. % to about 45 wt. %.

20. The method of claim 1, wherein the aging companion animal is geriatric.

* * * * *